US007897358B2

(12) United States Patent
Qin et al.

(10) Patent No.: US 7,897,358 B2
(45) Date of Patent: Mar. 1, 2011

(54) CANINE TRANSIENT RECEPTOR POTENTIAL V2 (CTRPV2) AND METHODS OF SCREENING FOR TRPV2 CHANNEL MODULATORS

(75) Inventors: Ning Qin, Blue Bell, PA (US); Christopher M. Flores, Lansdale, PA (US); Michael P. Neeper, Collegeville, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 170 days.

(21) Appl. No.: 12/042,016

(22) Filed: Mar. 4, 2008

(65) Prior Publication Data
US 2009/0165151 A1 Jun. 25, 2009

Related U.S. Application Data

(60) Provisional application No. 60/893,445, filed on Mar. 7, 2007.

(51) Int. Cl.
*C12N 15/12* (2006.01)
*G01N 33/567* (2006.01)
*C07K 14/705* (2006.01)

(52) U.S. Cl. ..... 435/7.2; 435/7.21; 435/69.1; 435/252.3; 435/320.1; 536/23.5

(58) Field of Classification Search .......................... None
See application file for complete search history.

(56) References Cited

U.S. PATENT DOCUMENTS
7,575,882 B2   8/2009   Qin et al.

FOREIGN PATENT DOCUMENTS
EP      1160254 A    12/2001
WO   WO 2006/005471 A    1/2006
WO   WO 2007/053526 A    5/2007

OTHER PUBLICATIONS

Database NCBI, May 30, 2005, XP002495693 accession No. XM 546641.
International Search Report dated Oct. 9, 2008 for International Appln. No. PCT/US2008/055782.
Aley et al., "Vincristine Hyperalgesia in the Rat: A Model of Painful Vincristine Neuropathy in Humans," *Neuroscience*, 1996; 73(1):259-265.
Bennett et al., "A Peripheral Mononeuropathy in Rat that Produces Disorders of Pain Sensation Like Those Seen in Man," *Pain*, 1988; 33:87-107.
Brennan et al., "Characterization of a Rat Model of Incisional Pain," *Pain*, 1996; 64:493-501.
Calcutt et al., "Spinal Pharmacology of Tactile Allodynia in Diabetic Rats," *British Journal of Pharmacology*, 1997; 122:1478-1482.
Caterina et al., "The Capsaicin Receptor: A Heat-Activated Ion Channel in the Pain Pathway," *Nature*, 1997; 389:816-824.
Caterina et al., "A Capsaicin-Receptor Homologue with a High Threshold for Noxious Heat," *Nature*, 1999; 398:436-441.
Caterina et al., "Impaired Nociception and Pain Sensation in Mice Lacking the Capsaicin Receptor," *Science*, 2000; 288:306-313.
Cavaletti et al., "Experimental Peripheral Neuropathy Induced in Adult Rats by Repeated Intraperitoneal Administration of Taxol," *Experimental Neurology*, 1995; 133:64-72.
Chacur et al., "A New Model of Sciatic Inflammatory Neuritis (SIN): Induction of Unilateral and Bilateral Mechanical Allodynia Following Acute Unilateral Peri-Sciatic Immune Activation in Rats," *Pain*, 2001; 94:231-244.
Cole et al., "The EBV-Hybridoma Technique and its Application to Human Lung Cancer," *Monoclonal Antibodies and Cancer Therapy*, 1985; 77-96. Alan R. Liss, Inc.
D'Amour et al., "A Method for Determining Loss of Pain Sensation," *J. Pharmacol.*, 1941; 72:74-79.
Davis et al., "Vanilloid Receptor-1 is Essential for Inflammatory Thermal Hyperalgesia," *Nature*, 2000; 405:183-187.
Decosterd et al., "Spared Nerve Injury: An Animal Model of Persistent Peripheral Neuropathic Pain," *Pain*, 2000; 87:149-158.
Eddy et at, "Synthetic Analgesics: I. Methadone Isomers and Derivatives," *J. Pharmacol. Exp. Ther.*, 1950; 98(2):121-137.
Fleetwood-Walker et al., "Behavioural Changes in the Rat Following Infection with Varicella-Zoster Virus," *J. Gen. Virol.*, 1999; 80:2433-2436.
Giannoni et al., "Efficient One-Tube RT-PCR Amplification of Rare Transcripts Using Short Sequence-Specific Reverse Transcription Primers," *BioTechniques*, 1995; 18(2):204-206.
Giannoni et al., "An Improved Reverse Transcription-Polymerase Chain Reaction Method to Sutdy Apolipoprotein Gene Expression in Caco-2 Cells," *Journal of Lipid Research*, 1994; 35(2):340-350.
Hargreaves et al., "A New and Sensitive Method for Measuring Thermal Nociception in Cutaneous Hyperalgesia," *Pain*, 1988; 32:77-88.
Hunskaar et al., "Formalin Test in Mice, a Useful Technique for Evaluating Mild Analgesics," *Journal of Neuroscience Methods*, 1985; 14:69-76.
Kanzaki et al., "Translocation of Calcium-Permeable Cation Channel Induced by Insulin-like Growth Factor-I," *Nature Cell Biology*, 1999; 1:165-170.
Kim et al., "An Experimental Model for Peripheral Neuropathy Produced by Segmental Spinal Nerve Ligation in the Rat," *Pain*, 1992; 50:355-363.
Kohler et al., "Continuous Cultures of Fused Cells Secreting Antibody of Predefined Specificity," *Nature*, 1975; 256:495-497.
Kozbor et al., "The Production of Monoclonal Antibodies from Human Lymphocytes," *Immunology Today*, 1983; 4(3):72-79.
Lam, K.S., "Application of Combinatorial Library Methods in Cancer Research and Drug Discovery," *Anti-Cancer Drug Design*, 1997; 12:145-167.
Merrifield et al., "Solid Phase Peptide Synthesis. I. The Synthesis of a Tetrapeptide," *J. Am. Chem. Soc.*, 1963; 85(14):2149-2154.
Milligan et al., "Thermal Hyperalgesia and Mechanical Allodynia Produced by Intrathecal Administration of the Human Immunodeficiency Virus-1 (HIV-1) Envelope Glycoprotein gp120," *Brain Research*, 2000; 861:105-116.
Muraki et al., "TRPV2 is a Component of Osmotically Sensitive Cation Channels in Murine Aortic Myocytes," *Circ. Res.*, 2003; 93(9):829-838.

(Continued)

*Primary Examiner* — John D Ulm
(74) *Attorney, Agent, or Firm* — Patton Boggs, LLP

(57) ABSTRACT

A recombinant canine TRPV2 channel which has been prepared by cDNA cloning and polymerase chain reaction techniques is disclosed. Expression systems for these channels and an assay using the expression systems are also disclosed. The recombinant TRPV2 channel can be used in assays to evaluate compounds which directly or indirectly interact with or bind to TRPV2 channel.

29 Claims, 12 Drawing Sheets

OTHER PUBLICATIONS

Needleman et al., " A General Method Applicable to the Search for Similarities in the Amino Acid Sequence of Two Proteins," *J. Mol. Biol.*, 1970; 48:443-453.

Nozaki-Taguchi et al., "Vincristine-Induced Allodynia in the Rat," *Pain*, 2001; 93:69-76.

Randall et al., "A Method for Measurement of Analgesic Activity on Inflamed Tissue," *Arch. Int Pharmacodyn*, 1957; 111:409-419.

Sandy et al., "Mammalian RNAi: A Practical Guide," *Biotechniques*, 2005; 39(2):215-224.

Shir et al., "A-Fibers Mediate Mechanical Hyperesthesia and Allodynia and C-Fibers Mediate Thermal Hyperalgesia in a New Model of Causalgiform Pain Disorders in Rats," *Neuroscience Letters*, 1990; 115:62-67.

Siegmund et al., "A Method for Evaluating Both Non-Narcotic and Narcotic Analgesics," *Proc. Soc. Exp. Bio. Med.*, 1957; 95:729-731.

Tominaga et al., "The Cloned Capsaicin Receptor Integrates Multiple Pain-Producing Stimuli," *Neuron*, 1998; 21(3):531-543.

Figure 1A

```
                                                                                          -13 acgcggggggtagg
  1  ATGGCCTCGC CCTCCAGCTC TCCCACTTTC AGCCTTGAGA CATCAGATGG AGGCCAGGAA GATGGCAGTG AGGTGGACAA AAGAAAGGCT GGCCCGGGGG
     TACCGGAGCG GGAGGTCGAG AGGGTGAAAG TCGGAACTCT GTAGTCTACC TCCGGTCCTT CTACCGTCAC TCCACCTGTT TTCTTTCCGA CCGGGCCCCC
     M  A  S  P  S  S  S  P  T  F  R  L  E  T  S  D  G  Q  E  D  G  S  E  V  D  K  R  K  A  G  P  G  A 101  CTGGCCACC CCCCATGGAG TCACCATTCC AAGGGAGCA TCGCAAATGC TCTCCTCAGA TCAAAGTAAA CCTCAACTTC CGCAAAGGAG CAGGTGTCAG
     GACCCGGTGG GGGGTACCTC AGTGGTAAGG TTCCCCTCCT AGCGTTTACG AGAGGAGTCT AGTTTCATTT GGAGTTGAAG GCGTTTCCTC GTCCACAGTC
     . G  P  P  . P  M  E  S  P  F  . Q  G  E  D  R  K  C  S  P  Q  I  K  V  N  L  N  F  R  K  G  A  G  V  S 201  CCAGCCGGAC CCAAACCGCT TTGACCGGTGA TCGGCTCTTC AGCCTGGGTTG CCCGGGGTGT CCCCGAGGAT CTGGCTGGGT TACCAGAGTA CCTGTCCCGG
     GGTCGGCCTG GGTTTGGCGA AACTGGCACT AGCCGAGAAG TCGGACCAAC GGGCCCCACA GGGGCTCCTA GACCGACCCA ATGGTCTCAT GGACAGGGCC
     . Q  P  D  P  N  R  F  D  R  D  R  L  F  S  V  V  A  R  G  V  P  E  D  L  A  G  L  P  E  Y  L  S  R 301  ACCAGCCAAGT ACCTCACCGA CTCAGAGTAC ATGAAGGCTG TGTTAAACCT TCGGGATGGT GCCAACGCCT
     TGGTCGTTCA TGGAGTGGCT GAGTCTCATG TACTTCCGAC ACAATTTGGA AGCCCTACCA CGGTTGCGGA
     . T  S  K  Y  L  T  D  S  E  Y  M  K  A  V  L  N  L  R  D  G  A  N  A  C 401  GCAGCCTGCC ATTGCTTCAG ATCGACCGGA ACTCTGGCAA TCCCCAGCCC CTGGTCAATG CCCAATGCAC GGATGAGTAC TACCGAGGCC ACAGTGCCCT
     CGTAGGACGG TAACGAAGTC TAGCTGGCCT TGAGACCGTT AGGGGTCGGG GACCAGTTAC GGGTTACGTG CCTACTCATG ATGGCTCCGG TGTCAGGGA
     . I  L  P  L  I  Q  I  D  R  N  S  G  N  P  Q  P  L  V  N  A  Q  C  T  D  E  Y  Y  R  G  H  S  A  L 501  GCATATGCC ATCGAGAAGA GGAGCCTGCA GTGTGTGAAG CTCTTGGTG AGAACGGGGC CAATGTGCAT GCCCAGCCCT GTGGCCAATT CTTCCAGAAA
     CGTATAACGG TAGCTCTTCT CCTCGGACGT CACACACTTC GAGAACCAC GTTGCCCCG GTTACACGTA CGGGTCGGGA CACCGGTTAA GAAGGTCTTT
     . H  I  A  T  E  K  R  S  L  Q  C  V  K  L  L  V  E  N  G  A  N  V  H  A  Q  C  Q  P  F  Q  K 601  AAGAGCCAAG GGACTTGCTT CTACTTTGGT GAGCTGCCCC CTGAACGAA CTGGAGAGACCG ATGGAGGAC CTCTTGGGCG
     TTCTCGGTTC CCTGAACGAA GATGAAGTC ACGGACGTC TAGACACTG CTGCTGGAC GACTACCACTG CGATAGCC GAGAACCCGC
     K  S  Q  G  T  C  F  Y  F  G  E  L  P  L  S  L  A  A  C  T  K  Q  W  D  V  V  T  Y  L  L  E  N  P  H 701  ATCAGCCTGC CAGCCTGCAG GCAGCCCGACT CGCTGGGCAA CGGCCCCTG CATGCCCTTGG TGATGATCGC AGACAACTCA GCCGAGAACA GTGCCCTGGT
     TAGTCGGACG GTCGGACGTC CGTCGGCTGA GCGACCCGTT GCCGGGGAC GTACGGGAACC ACTACCAGCG TCTGTTGAGT CGGCTCTTGT CACGGGACCA
     . Q  P  A  S  L  Q  A  A  D  S  L  G  N  A  L  H  A  L  V  M  I  A  D  N  S  A  E  N  S  A  L  V 801  GATCCGCATG TATGATGCG CTCCTCCGTGC TGGGGCCCGC AAGTGCCCA CGAGGACATC CCCAACCTGC AGGGGCCTCAC GCCCCTGAAG  (1)
     CTAGGCGTAC ATACTACCG GAGGAGGCACG ACCCCGGGCG TTCAGCGT GCTCCTGTGA GGGTTGGACG TCCCGGAGTG CGGGGACTTC  (2)
     . I  R  M  Y  D  A  L  L  R  A  G  A  R  L  C  P  K  V  Q  L  E  D  I  P  N  L  Q  G  L  T  P  L  K  (3)
```

(1) (nucleotides 1-913 of SEQ ID NO: 1)
(2) (complementary binding nucleotides to nucleotides 14-913 of SEQ ID NO: 1)
(3) (amino acids 1-300 of SEQ ID NO: 2)

Figure 1B

```
 901 CTGGCTGCCA AGGAGGGCAA AATCGAGATT TCAGGCACA TCCTGCAGCG GGAGTTCTCG GGGCCCGTGCC AGTCACTTTC CGGAAAGTTT ACTGAGTGGT
     GACCGACGGT TCCTCCCGTT TTAGCTCTAA AGTCCGTGT AGGACGTCGC CCCTCAAGAGC CCCGGCACGG TCAGTGAAAG GGCTTTCAAA TGACTCACCA
      L  A  A  K  E  G  K   T  E  I   P  R  H   I  L  Q  R   E  F  S   G  P  C  Q   G  S  L  S   R  K  F   T  E  W  C

1001 GCTACGGGCC TGTCCGGGTG TGCGTGATG ACCTGGCCTC TGTGGAACAGC ACTCCGTGCT GGAGATCATC GCCTTTCATT GCAGAAGCCC
     CGATGCCCGG ACAGGCCCAC ACGCACTAC TGGACCGGAG ACACCTTGTCG TGAGGCACGA CCTCTAGTAG CGGAAAGTAA CGTCTTCGGG
      . Y  G  P   V  R  V   S  L  Y  D   L  A  S   V  D  S   W  E  E  N   S  V  L   E  I  I   A  F  H  C   R  S  P .

1101 GCACCGACAC CGAATGGTGG TTTTGGAACC ACTGAACAAA CGCTACAGG CGAATATGGA TCTGCTAATC CCCAGATTCT TCTTCAACTT CCTGTGTTAC
     CGTGGCTGTG GCTTACCACC AAAACCTTGG TGACTTGTTT GCGATGTCC GCTTACCCT AGACGATTAG GGGTCTAAGA AGAAGTTGAA GGACACAATG
      . H  R  H   R  M  V   L  E  P   L  N  K   L  L  Q   A  K  W  D   L  L  I   P  R  F  F   F  N  F   L  C  Y .

1201 CTGACCTACA TGTTCATCTT TACCCGTGTT GCTTACCACC AGCCAGCCCT GGGGAAGGCC TTCCTCCCCC CGACTGTGAC TACTGGGGAC TCCATGCTGC
     GACTGGATGT ACAAGTAGAA ATGGGCACAA CGAATGGTGG TCGGTCGGGA CCCCTTCCGG AAGGAGGGGG GCTGACACTG ATGACCCCTG AGGTACGACG
      . L  T  Y   M  F  I  F   T  R  V   A  Y  H  Q   P  A  L   G  K  A   F  L  P  P   T  V  T   T  G  D   S  M  L  L

1301 TGGTGGGCCA CATCGGATC CTCCTTGGGG GGGTCTACCT CTTGGTGGGC CAGCTATGGT CCCGCGTCTG TTCATCTGGA TCTCCTTCGT
     ACCACCCGGT GTACGACTAG GAGGAACCCC CCCAGATGGA GAACCGCGGG GTCGATACCA CGCACAGAC ACGTAGACCT AGAGGAAGCA
      . L  G  H   I  L  I   L  L  G  G   V  Y  L   L  V  G   Q  L  W  Y   P  V  R   R  R  L   F  I  W  I   S  F  V .

1401 GGAACAGCTAC TTTGAACTGG TCTTCCAGGT CCAGGCCCTG CTCACAGTGC TGTCCCAGGG ACTGTGTTTC CTGGCCGTGG AGTGGTACCT GCCTCTGCTT
     CCTTGTCGATG AAACTTGACC AGAAGGACCA GGTCCGGGAC GAGTGTCACG ACAGGGTCCC TGACACAAAG GACCGGCACC TCACCATGGA CGGAGACGAA
      . D  S  Y   F  E  L  L   V  F  Q   V  Q  A  L   L  T  V  L   S  Q  G   L  C  F   L  A  V  E   W  Y  L   P  L  L

1501 GTGTCTTCCC TGGTGCTGGG ACCACGAGGG CTGGCTGAAC CTTGCAGCGC ACAGGCCATC ACAGTCGAGTCTCT GATCCAGAAG GTCATCCTGC
     CACAGAAGGG ACCACGACCC TGGTGCTCCC GACCGACTTG GAACGTCGCG TGTCCGGTAG TGTCAGCTC AGTAGGACGC CTAGGACGAC CAGTAGGACG
      V  S  S   L  V  L  G   W  L  N   L  L  Y   Y  T  R  G   L  Q  H   T  G  I  Y   S  V  M   I  Q  K   V  I  L  R

1601 GGGAACCTGCT CCGGTTCCTG AGGCAGGAGA AATGTCACGG CTGTTGGCTTC TAGTCTTCC GTTTGGAGCCT TGGTGAGCCT GAGCCGGGAA GCCCGAGACT CTGGGGTCCC
     CCCTGGACGA GGCCAAGGAC TCCGTCCTCT TTACAGTGCC GACCAAGAAG ATCAGAAGGA CAAACCGAAG CGACACTCGGA CCACTCGGCC CTCGGGCCTT CGGGCTCTGA GACCCCAGGG
      . D  L  L   R  F  L   L  V  Y  L   V  F  L   F  G  F   A  V  A  L   V  S  L   S  R  E   A  R  D  S   G  V  P .

1701 CACAGGCCCC AATGTCACGG AGGAGGCGCA GTCTGGGGCA GGACAGGGGG ACCAGGAGGG CAGTCCTCCC CCATACGGTG GCATACTGGA CGCTTCCTTG
     GTGTCCGGGG TTACAGTGCC TCCTCCGCGT CAGACCCCGT CCTGTCCCCC TGGTCCTCCC GTCAGGAGG GGTATGCCAC CGTATGACCT GCGAAGGAAC
      . T  G  P   N  V  T  E   A  A  Q   S  G  A   G  Q  G  L   E  E  G   S  S  S   P  Y  G  G   I  L  D   A  S  L

1801 GAGCTCTTCA AGTTCACCAT CGGCATGGGG GAGCTGGCAT TCCAAGACCA AGCTGCCTTC CGGCGCGTGG TGCTACTGCT GTTCCTGGCC TATGTGCTGC (1)
     CTCGAGAAGT TCAAGTGGTA GCCGTACCCC CTCGACCGTA AGGTTCTGGT TCGACGGAAG GCCGCGCACC ACGATGACGA CAAGGACCGG ATACACGACG (2)
      E  L  F  K   F  T  I   G  M  G   E  L  A  F   Q  D  Q   L  A  F   R  G  V  V   L  L  L   L  F  L  A   Y  V  L  L . (3)
```

(1) (nucleotides 914-1913 of SEQ ID NO: 1)
(2) (complementary binding nucleotides to nucleotides 914-1913 of SEQ ID NO: 1)
(3) (amino acids 301-634 of SEQ ID NO: 2)

Figure 1C

```
1901  TCACTTACAT CCTGCTGCTC AATATGCTCA TCGCCCTCAT GAGCGAGACC GTCAACAGTG TTGCCAGTGA CAGCTGGAGC ATCTGGAAGC TGCAGAAAGC
      AGTGGATGTA GGACGACGAG TTATACGAGT AGCGGGAGTA CTCGCTCTGG CAGTTGTCAC AACGGTCACT GTCGACCTCG TAGACCTTCG ACGTCTTTCG
      .  T  Y  I  L  L  N  M  L  I  A  L  M  S  E  T  V  N  S  V  A  S  D  S  W  S  I  W  K  L  Q  K  A  .

2001  TATCTCTGTC CTGGAGATGG AGAATGGCTA CTGGTGGTGC AGGAGGAAGA AGCAGGCGGGC CGGTGTGAAAG CTGACCGTTG GGACCAGGCC GGATGGTAGC
      ATAGAGACAG GACCTCTACC TCTTACCGAT GACCACCACG TCCTCCTTCT TCGTCGCCCG GCCACACTTC GACTGGCAAC CCTGGTCCGG CCTACCATCG
      .  I  S  V  L  E  M  E  N  G  Y  W  W  C  R  R  K  K  Q  R  A  G  V  K  L  T  V  G  T  R  P  D  G  S

2101  TCTGATGAGC GCTGGTGCTT CAGGGTGGAG GAAGTGAACT GGGCTGCGTG TGTGTGAAGA GCCATCAGGC CCAGCTGTCC
      AGACTACTCG CGACCACGAA GTCCCACCTC CTTCACTTGA CCCGACGCAC GACGGTTGTC ACACACTTCT CGGTAGTCCG GGTCGACAGG
      S  D  E  R  W  C  F  R  V  E  E  V  N  W  A  A  W  E  Q  T  L  P  T  V  C  E  E  P  S  G  P  A  V

2201  CTGGCAGCAT AAGGAACCCT GTCCTGGCCT CCCAACCGGA GGAGGACACT GCCTCGGAGG AAGACCAACT GCCCCTCCAG CTCCTGAAGT CCCACTAATG
      GACCGTCGTA TTCCTTGGGA CAGGACCGGA GGGTTGGCCT CCTCCTGTGA CGGAGCCTCC TTCTGGTTGA CGGGGAGGTC GAGGACTTCA GGGTGATTAC
      P  G  S  I  R  N  P  V  L  A  S  Q  P  E  E  D  T  A  S  E  E  D  Q  L  P  L  Q  L  L  K  S  H  *    (3)

2301  GCCCAGTTGC ACGGCAGTCA GGAAATCTTC CCAGCCCTGC TGGGGCTCCA GAGAACTTTG GTGGCAAATG TAAATAAATA TCTTTTCATA
      CGGGTCAACG TGCCGTCAGT CCTTTAGAAG GGTCGGGACG ACCCCGAGGT CTCTTGAAAC CACCGTTTAC ATTTATTTAT AGAAAAGTAT

2401  AAAAAAAAAA AAAAAAAAAA   (1)
      TTTTTTTTTT TTTTTTTTTT   (2)

(1)  (nucleotides 1914-2443 of SEQ ID NO: 1)
(2)  (complementary binding nucleotides to sequences 1914-2443 of SEQ ID NO: 1)
(3)  (amino acids 635-765 of SEQ ID NO: 2)
```

```
hTRPV2     1 atgacctcacctccagctctccagttttcaggttggagacattagatgg    50
               |||  |||| |||||||||||||||||| |||||||||||||||||||||
cTRPV2     1 atggctcgcctccagctctccactttcaggctgagacatcagatgg      50 hTRPV2    51 aggccaagaagatggctctgaggcggacagagaaagctggatttggga   100
               ||||||||||||||||||||||||| ||||||||||| ||||||| |
cTRPV2    51 aggccaggaagatgaagtgagtggacaaaagaaaaggctggcccggggg   100 hTRPV2   101 gcgggctgcctggagtcacagttccagggcgaggacctggaaattc     150
               |||||||||||||| |||||||||||||| ||||||||| |||
cTRPV2   101 ctgggccaccccccatggagtcaccattccaaggggaggatcgcaaatgc   150 hTRPV2   151 gccctcagataagagtcaacctcaactaccgaaaggaacaggtgccag   200
               ||||||||||| |||||| |||||| |||||||||||||||||||| 
cTRPV2   151 tctcctcagatcaaagtaaacctcaacttccgcaaggaggcaggtcag   200 hTRPV2   201 tcagccggatccaaaccgatttgaccgagatcggctcttcaatgcggtct   250
               |||| ||||||||||||| |||| |||| |||||||||||||| ||| 
cTRPV2   201 ccagccggacccaaaccgcgttgaccgttgatcggctcttcagcggttg   250 hTRPV2   251 cccgggtgtccccgaggatctgctggactgtgctcagagtacctgagcaag   300
               || |||||||||||||||||||||||||| |||||||||| ||||||||
cTRPV2   251 cccggggtgtccccgaggatctgctgctggttaccagagtacctgtcccg   300 hTRPV2   301 accagcaagtacctcaccgactcagagtacagagagggctccacaggtaa   350
               ||||| |||||||||||||||||||||||||||| ||||||||||| |
cTRPV2   301 accagcaagtacctcaccgactcagagtacagagggctccacaggcaa   350 hTRPV2   351 gacgtgcctgatgaagcttaaggacggagtcaatgcct              400
               |||||||||||||||| |||| |||| ||||| ||||| 
cTRPV2   351 gacgtgcctgatgaaggctgtgttaaacttcgggatgtggtgccaacgcct  400 hTRPV2   401 gcattctgccactgctgcagatcgacaggactctggcaatcctcagccc    450
               |||| |||||||||||||| |||||||||||||| |||||||||||||
cTRPV2   401 gcatcctgccattgcttcagatcgacaggaactctggcaatccccagccc  450
```

(nucleotides 1-450 of SEQ ID NO: 3)

(nucleotides 1-450 of SEQ ID NO: 1)

Figure 3B

```
hTRPV2  451 ctggtaaatgcccagtgcacagatgactattaccgaggccacagcgctct 500
cTRPV2  451 ctggtcaatgcccaatgcacggatgagtactaccgaggccacagtgccct 500
hTRPV2  501 gcacatcgccattgagaacaggagtctgcagtgtgtgaagctcctggtgg 550
cTRPV2  501 gcatattgccatcgagaagaggagcctgcagtgtgtgaagctcttggtgg 550
hTRPV2  551 agaatgggccaatgtgcaatgcccggggcctgcgggccgcttcttccag... 597
cTRPV2  551 agaacggggccaatgtgcaatgcccaggccctgtggccaattcttccagaaa 600
hTRPV2  598 aagggccaagggactttatttcgtgtgagctaccccctctctttggc 647
cTRPV2  601 aagagccaagggacttgcttctactttggtgagctgccctctctctggc 650
hTRPV2  648 cgcttgcaccaagccagcagtggatgtggtaagctacctcctggagaacccac 697
cTRPV2  651 tgcgtgcaccaagccagtgcagtgggatgtggtgacctacctcctggagaaccccgc 700
hTRPV2  698 accagcccgcagcctgcagcctgactgcccactgacttcccaggcaacacagtcctg 747
cTRPV2  701 atcagcgcatgcagcctgcagcctgactcgctgggcagcagtgcccctg 750
hTRPV2  748 catgcctagtgatgatgatctcggacaactcagctgagaacattgcactggt 797
cTRPV2  751 catgccttggtgatgatcgcagacaactcagccagccaactgcccctggt 800
hTRPV2  798 gaccagcatgtatgatgatggctcctccaagcccctcgcgcctctgccta 847
cTRPV2  801 gatccgcatgtatgatggacatcggctccttcgtgctgggccgcctctgccca 850
hTRPV2  848 ccgtgcagcttgaggacatccgaggacctgagactctcacgcgcctctgaag 897
cTRPV2  851 aagtgcagctcgaggacatcccaacctgcaggcctcacgcgccctgaag 900
hTRPV2  898 ctggcccgccaaggagggcaagatttcaggcacatcctgcagcg 947
cTRPV2  901 ctggctgccaaggagggcaaaatcgagatttcaggcacatcctgcagcg 950
```

(nucleotides 451-947 of SEQ ID NO: 3)
(nucleotides 451-950 of SEQ ID NO: 1)

Figure 3C (nucleotides 948-1444 of SEQ ID NO: 3)
(nucleotides 951-1447 of SEQ ID NO: 1)

```
hTRPV2   948  ggagtttttcaggactgagcca...cctttcccgaaagttcaccgagtggt  994
cTRPV2   951  ggagttctcggggccgtgccagtcacttcccgaaagttactgagtggt     1000
hTRPV2   995  gctatgggcctgtccggtgtcgctgtatgacctggcttctgtgtgacagc   1044
cTRPV2  1001  gctacgggcctgtccggtgtcgctgtatgacctggcctctgtgtgacagc   1050
hTRPV2  1045  tgtgaggagaactcagtgctggagatcattgcctttcattgcaagagccc   1094
cTRPV2  1051  tgggaggagaactccgtgctggagatcatcgcctttcattgcagaagccc   1100
hTRPV2  1095  gcaccgacaccgaatgtcgtttggagccctgaacaaactgctgcagg     1144
cTRPV2  1101  gcaccgacaccgaatggtggtttggagaaccactgaacaaactgctacagg  1150
hTRPV2  1145  cgaaatgggatctgctcatcccaagttcttcttaaacttcctgtgtaat    1194
cTRPV2  1151  cgaaatgggatctgctaatcccagattcttcttcaacttcctgtgttac   1200
hTRPV2  1195  ctgatctacatgttcatcttcaccgctgttgctaccaccatcagccactaccct  1244
cTRPV2  1201  ctgacctacatgttcatcttcaccttaccgctgttgctaccaccagccct   1250
hTRPV2  1245  gaagaagcaggccgcgccctcacctgaaagcgaaggttggaaactccatgc  1294
cTRPV2  1251  gggga...aggccttcctcccccccgactgtgactactggggactccatgc  1297
hTRPV2  1295  tgctgacgggccacatccttatcctaggggggatctacctgtaccctcgtg 1344
cTRPV2  1298  tgctgctgggccacatccttcctgatcctcctggggggggtctacctggtg 1347
hTRPV2  1345  ggccagctgtgtgtactttctggcgcgccacgtgttcatctggatctcgtt  1394
cTRPV2  1348  ggccagctatgtgtactttctggaggcgtcgtctgttcatctggatctcctt 1397
hTRPV2  1395  catagacagcagctactttgaaatcctcctgttccaggccctgctcacag   1444
cTRPV2  1398  cgtggacagcagctactttgaactgctcttcctggtcctgctcacacag   1447
```

Figure 3D

```
hTRPV2  1445 tggtgtccaggtgctgtgtttcctggccatcgagtggtacgccctg     1494
cTRPV2  1448 tgctgtcccaggactgtgttgctgggctggagtggtacgcctctg     1497
hTRPV2  1495 cttgtgtctgcgctggtgctggtgctgaacctgctcttactatacacg   1544
cTRPV2  1498 cttgtgtcttccctgctgggctggtgctgaacctgctctattacacg    1547
hTRPV2  1545 tggcttccagcacacaggcatctacagtgtcatgatccagaaggtcatcc 1594
cTRPV2  1548 cggcttgcagcacacaggcatctacagtgtcatgatccagaaggtcatcc 1597
hTRPV2  1595 tgcgggacctgtgcgctccgcttcctctgatctacttagtcttccttttcggc 1644
cTRPV2  1598 tgcgggacctgtcccgcttcctctgctgttctacttagtcttcctgttggc  1647
hTRPV2  1645 ttcgctgtagccctggtgagcctgaggaggcttggcgccccgaagc     1694
cTRPV2  1648 ttcgctgtagccctggtgagcctgaagcctgagacctctgggt        1697
hTRPV2  1695 tcctacaggcccaatgccacagagtcagtgcagcccagtgcagccagg   1744
cTRPV2  1698 cccacaggcccaatgtccacggaggcagcgcagtctggggcaggacagg  1747
hTRPV2  1745 aggac...gagggcaacgggggcccagtacacagggtatcctggaagcctcc 1791
cTRPV2  1748 gggacgaggagggcagctccctcccccatacggtgtggcatactgacgcttcc 1797
hTRPV2  1792 ttggagctctcaaattcaccatcaccatggcatgggcgagctggccctttccagga 1841
cTRPV2  1798 ttggagctcttcaagttcaccatcggcatgggggagctggcttggcattccaaga 1847
hTRPV2  1842 gcagctgcacttccgcggcattgtgctgctgctgctgctggctacgtgc  1891
cTRPV2  1848 ccagctgcgcttccgcggccgtgctgttgtctcctggcctatgtgtgc   1897
hTRPV2  1892 tgctcacctacatcctgctgctcaacatgctcatcgccctcatgagcgag 1941
cTRPV2  1898 tgctcacttacatcctgctgctcaatatgctcatcgccctcatgagcgag 1947
```

(nucleotides 1445-1941 of SEQ ID NO: 3)
(nucleotides 1448-1947 of SEQ ID NO: 1)

Figure 3E

```
hTRPV2  1942  accgtcaacagtgtcgccactgacagctgaagcatctggaagctgcagaa        1991
              ||||||||||||||||||||||||||||||||||||||||||||||||||
cTRPV2  1948  accgtcaacagtgttgccagtgacacagctgaagcatctggaagctgcagaa       1997 hTRPV2  1992  agccatctctgtcctggagatggagaatggctattggttggtgc...agga        2038
              ||||||||||||||||||||||||||||||||||||||||||||   ||||
cTRPV2  1998  agctatctctgtcctggagatggagaatggctactggtgtgcaggagga         2047 hTRPV2  2039  agaagcagcgggcaggtgtgatgctgacccgttggcactaagccagatggc        2088
              ||||||||||||||||||||||||||||||||||||||||||||||||||
cTRPV2  2048  agaagcagcgggccggtgtgtgaactgacgttgggaccaggccggatggt        2097 hTRPV2  2089  agcccgatgagcgctggctgtgcctcagggtggagaggtgaactggcttc        2138
              ||||||||||||||||||||||||||||||||||||||||||||||||||
cTRPV2  2098  agctctgatgagcgctggtgtgcttcagggtggagaagtgaactgggctgc        2147 hTRPV2  2139  atgggagcagacgctgcctacgctgtgtgagagcccgtcaggggcaggtg        2188
              ||||||||||||||||||||||||||||||||||||||||||||||||||
cTRPV2  2148  gtgggagcagacgctgcaacagtgtgtgaagagccatcaggcccagctg         2197 hTRPV2  2189  tcccctcgaactctcgagaacccctggcttcccctcccaaggaggagat        2238
              ||||||||||||||||||||||||||||||||||||||||||||||||||
cTRPV2  2198  tccctggcagcataaggaacccctgtcctggcctcccaacc......ggag       2241 hTRPV2  2239  gaggatggtgcctctgaggagaaaactatgtgcccgtccagctcctccagtc     2288
              ||||||||||||||||||||||||||||||||||||||||||||||||||
cTRPV2  2242  gaggacactgcctccggaggaggaaccaactgccccctccagctcctgaagtc     2291 hTRPV2  2289  caactga 2295      (nucleotides 1942-2288 of SEQ ID NO: 3)
              ||||| |
cTRPV2  2292  ccactaa 2298      (nucleotides 1948-2291 of SEQ ID NO: 1)
```

Figure 4

Percent Similarity: 87.0   Percent Identity: 84.2

```
hTRPV2    1 MTSPSSSPVFRLETLDGGQEDGSEADRGKLDFGSGLPPMESQPQGEDRKF  50
            | ||||||| ||||| ||||||||| |: |   |.| |||||  ||||||
cTRPV2    1 MASPSSSPTFRLETSDGGQEDGSEVDKRKAGPGAGPPPMESPPQGEDRKC  50 hTRPV2   51 APQIRVNLNYRKGTGASQPDPNRFDRDRLFNAVSRGVPEDLAGLPEYLSK 100
            .|||:||||:||  |  ||||||||||||||||. |.||||||||||||:
cTRPV2   51 SPQIKVNLNFRKGAGVSQPDPNRFDRDRLFSVVARGVPEDLAGLPEYLSR 100 hTRPV2  101 TSKYLTDSEYTEGSTGKTCLMKAVLNLKDGVNACILPLLQIDRDSGNPQP 150
            |||||||||||||||||||||||||||:|| |||||||||||.||||||
cTRPV2  101 TSKYLTDSEYTEGSTGKTCLMKAVLNLRDGANACILPLLQIDRNSGNPQP 150 hTRPV2  151 LVNAQCTDDYYRGHSALHIAIEKRSLQCVKLLVENGANVHARACGRFFQ. 199
            ||||||||:|||||||||||||||||||||||||||||||.|||.|||
hTRPV2  151 LVNAQCTDEYYRGHSALHIAIEKRSLQCVKLLVENGANVHAQACGQFFK 200 hTRPV2  200 KGQGTCFYFGELPLSLAACTKQWDVVSYLLENPHQPASLQATDSQGNTVL 249
            | |||||||||||||||||||||||||||.|||||||||||  || | |
cTRPV2  201 KSQGTCFYFGELPLSLAACTKQWDVVTYLLENPHQPASLQAADSLGNTAL 250 hTRPV2  250 HALVMISDNSAENIALVTSMYDGLLQAGARLCPTVQLEDIRNLQDLTPLK 299
            ||||||.|||||| |||   ||||| ||||||||.||||||  || ||||
cTRPV2  251 HALVMIADNSAENSALVIRMYDALLRAGARLCPKVQLEDIPNLQGLTPLK 300 hTRPV2  300 LAAKEGKIEIFRHILQREFSG.LSHLSRKFTEWCYGPVRVSLYDLASVDS 348
            ||||||||||||||||||||| |||||||||||||||||||||||||||
cTRPV2  301 LAAKEGKIEIFRHILQREFSGPCQSLSRKFTEWCYGPVRVSLYDLASVDS 350 hTRPV2  349 CEENSVLEIIAPHCKSPHRHRMVVLEPLNKLLQAKWDLLIPKFFLNFLCN 398
            ||||||||||||:|||||||||||||||||||||||||||||:|| ||||
cTRPV2  351 WEENSVLEIIAPHCRSPHRHRMVVLEPLNKLLQAKWDLLIPRFFFNFLCY 400 hTRPV2  399 LIYMFIFTAVAYHQPTLKKQAAPHLKAEVGNSMLLTGHILILLGGIYLLV 448
            |||||||||||||| |  |    |.|||  ||||||||||||||||||||
cTRPV2  401 LTYMFIFTAVAYHQPALGKAFLPP.TVTTGDSMLLLGHILILLGGVYLLV 449 hTRPV2  449 GQLWYFWRRHVFIWISFIDSYFEILFLFQALLTVVSQVLCFLAIEWYLPL 498
            |||||||||| .|||||:|||||:|||| ||||||.|| ||||| ||||
cTRPV2  450 GQLWYFWRRRLFIWISFVDSYFELLFLVQALLTVLSQGLCFLAVEWYLPL 499 hTRPV2  499 LVSALVLGWLNLLYYTRGFQHTGIYSVMIQKVILRDLLRFLLIYLVFLFG 548
            |||.|||||||||||||||| ||||||||||||||||||||:|||||||
cTRPV2  500 LVSSLVLGWLNLLYYTRGLQHTGIYSVMIQKVILRDLLRFLLVYLVFLFG 549 hTRPV2  549 FAVALVSLSQEAWRPEAPTGPNATESVQPMEGQ.EDEGNGAQYRGILEAS 597
            ||||||||||.||  ||||| ||.| || ::||.  . | |||:||
cTRPV2  550 FAVALVSLSREARDSGVPTGPNVTEAAQSGAGQGDEEGSSSPYGGILDAS 599 hTRPV2  598 LELFKFTIGMGELAFQEQLHFRGMVLLLLAYVLLTYILLLNMLIALMSE 647
            |||||||||||||||||:|| |||.|||||||||||||||||||||||
cTRPV2  600 LELFKFTIGMGELAFQDQLRFRGVVLLLLAYVLLTYILLLNMLIALMSE 649 hTRPV2  648 TVNSVATDSWSIWKLQKAISVLEMENGYWWC.RKKQRAGVMLTVGTKPDG 696
            ||||||.|||||||||||||||||||||||| |||||||||:|||:|||
cTRPV2  650 TVNSVASDSWSIWKLQKAISVLEMENGYWWCRRKKQRAGVKLTVGTRPDG 699 hTRPV2  697 SPDERWCFRVEEVNWASWEQTLPTLCEDPSGAGVPRTLENPVLASPPKED 746
            | ||||||||||||||.|||||||.|| || ||   ::|||||| :
cTRPV2  700 SSDERWCFRVEEVNWAAWEQTLPTVCEEPSGPAVPGSIRNPVLASQP..E 747 hTRPV2  747 EDGASEENYVPVQLLQSN 764    (SEQ ID NO: 4)
            ||:||||. .|.|||.|.
cTRPV2  748 EDTASEEDQLPLQLLKSH 765    (SEQ ID NO: 2)
```

Figure 5

| Nucleotide Sequence | | | |
|---|---|---|---|
| | Human | Rat | Mouse |
| Canine | 86% | 82% | 83% |

| Amino Acid Sequence | | | |
|---|---|---|---|
| | Human | Rat | Mouse |
| Canine | 84% | 81% | 83% |

CANINE TRANSIENT RECEPTOR POTENTIAL V2 (CTRPV2) AND METHODS OF SCREENING FOR TRPV2 CHANNEL MODULATORS

CROSS REFERENCE TO RELATED APPLICATIONS

This application claims priority to Application No. 60/893,445 filed on Mar. 7, 2007, the entire contents of which are incorporated by reference herein.

FIELD OF THE INVENTION

The present invention relates to the canine TRPV2 (cTRPV2) channel, cloning of the channel, methods of screening for modulators of the TRPV2 channel and uses thereof.

BACKGROUND OF THE INVENTION

Both heat and cold evoke thermosensation, which, if of sufficient intensity, may elicit feelings of pain. Temperature detection in mammals is a critical function in the maintenance of thermal homeostasis and protection from potentially injurious temperature extremes. Considerable efforts have been put into elucidating the biochemical mechanisms involved in the detection, transduction and transmission of hot and cold sensations in neuronal tissues. Thermal stimuli activate specialized receptors located on sensory neurons, such as those deriving from the dorsal root ganglion (DRG) and the trigeminal ganglion (TG). When these stimuli are in the noxious range (i.e., very hot or cold), they activate a certain subset of thermo-sensitive receptors on a sub-population of sensory neurons called nociceptors (pain-sensing neurons). Upon activation, the thermo-sensitive receptors (e.g., ion channels) transduce the noxious stimulus into an electrical signal that is propagated along the sensory neuron to the spinal cord, where it is relayed to the brain, ultimately leading to the perception of pain. Accordingly, these thermo-sensitive receptors represent highly promising targets for developing drugs for the treatment of various painful conditions, particularly those in which thermal hypersensitivity and/or thermally evoked pain are present.

Several thermo-sensitive receptors have been implicated in sensing temperature changes. Currently, six members from the transient receptor potential (TRP) ion channel family have been proposed to serve as thermal sensors of temperatures ranging from noxious heat to noxious cold and thus are referred to as thermo-TRPs. The thermo-TRPs, which are non-selective cation channels, are also sensitive to chemical stimuli, such as capsaicin, menthol mustard oil, etc., which are known to produce a burning or cooling sensation. Importantly, all of the thermo-TRPs are expressed in nociceptive sensory neurons, either Aδ- or C-fibers, wherein thermo-, mechano- and chemo-sensory transduction take place. TRPV1, the most extensively characterized member of this family, is activated by moderate heat (~43° C.), capsaicin, protons and certain lipidic mediators, such as anandamide (Caterina, M. J., et al. 1997, *Nature* 389 (6653), 816-824; Tominaga, et al. 1998, *Neuron* 21(3), 531-543) Moreover, numerous studies using a variety of experimental approaches have implicated TRPV1 in the transduction of pain signals in animal models of hyperalgesia (Caterina, M. J., et al. 2000, *Science* 288(5464), 306-313; Davis, J. B., et al. 2000 *Nature* 405(6783), 183-187); hence, this TRP has been aggressively pursued as a target for the alleviation of certain types of pain.

The transient receptor potential V2 (TRPV2) protein (previously called and also known as vanilloid receptor-like 1 or VRL-1) is a member of the transient receptor potential (TRP) superfamily, which has been implicated in mediating diverse cellular functions, including the transduction of thermal, chemical and mechanical stimuli. TRPV2 is closely related to TRPV1 and was identified by homologous cloning from rat and human (Caterina et al., 1999, *Nature* 398(6726), 436-441) as well as mouse (Kanzaki, et al. 1999, *Nat Cell Biol* 1(3), 165-170). Functional studies have revealed that rat TRPV2 responds to noxious heat, with an activation threshold above 52° C. (Caterina, Rosen et al. 1999) and that mouse TRPV2 responds to changes in osmolarity or to membrane stretch (Muraki, et al. 2003, *Circ Res* 93(9), 829-838). The hypothesis that TRPV2 is an endogenous sensor of noxious heat and mechanical stretch is further supported by findings that it is expressed in medium to large diameter Aδ mechano- and thermo-sensory neurons in the dorsal root ganglion (DRG) (Caterina et al., 1999, *Nature* 398(6726), 436-441).

Unlike TRPV1, however, no selective activators of TRPV2 have been reported. Recently, a novel class of selective agonists, such as $\Delta^9$-tetrahydrocannabinol ($\Delta^9$-THC) as well as other related cannabinoids, that activate human, rat and mouse TRPV2 have been identified. (See U.S. application Ser. No. 11/589,340, entitled COMPOSITIONS AND METHODS FOR IDENTIFYING MODULATORS OF TRPV2 to Qin et al., filed Oct. 30, 2006, now U.S. Pat. No. 7,575,882, issued Aug. 18, 2009).

There is a need to identify additional thermo-sensitive receptors, as they are potential targets for the treatment of pain. There is also a need to identify thermo-sensitive receptors in different species, as they can be used as model systems to investigate the effects of test compounds. Particularly, there is a need for systems that can be used to test compounds that potentially increase or decrease the activity of a thermo-sensitive receptor responding to noxious thermal stimuli, including noxious heat. Identification and testing of such compounds would enable the treatment of various disorders associated with neuropathic pain, inflammatory pain, various chronic pains or for uses in other conditions, such as the inflammatory immune response, febrile seizures and general epilepsy and/or conditions in which thermal hypersensitivity or thermally evoked pain are present as well as other human diseases related to these thermo-sensitive receptors.

SUMMARY OF THE INVENTION

The present invention is directed to recombinant DNA and protein of canine TRPV2. The protein, which may be used in a high throughput assay, is useful to identify modulators of functional TRPV2. The present invention is also directed to modulators identified in the assays disclosed herein and their use as therapeutic agents.

Other aspects, features and advantages of the invention will be apparent from the following disclosure, including the detailed description of the invention and its preferred embodiments and the appended claims.

BRIEF DESCRIPTION OF THE FIGURES

FIGS. 1A-C illustrate the nucleotide sequence (SEQ ID NO: 1) and the protein translation (SEQ ID NO: 2) of canine TRPV2 cDNA, separately, FIG. 1A illustrates the nucleotide sequence (nucleotides 1-913 of SEQ ID NO: 1) and the protein translation sequence (amino acids 1-300 of SEQ ID NO: 2) of canine TRPV2 cDNA, FIG. 1B illustrates the nucleotide sequence (nucleotides 914-1913 of SEQ ID NO: 1) and the protein translation sequence (amino acids 301-634 of SEQ ID NO: 2) of canine TRPV2 cDNA, and FIG. 1C illustrates the nucleotide sequence (nucleotides 1914-2443 of SEQ ID NO: 1) and the protein translation sequence (amino acids 635-765 of SEQ ID NO: 2) of canine TRPV2 cDNA.

FIG. 2 illustrates the amino acid sequence of canine TRPV2 (SEQ ID NO: 2).

FIGS. 3A-E illustrate an alignment of the canine TRPV2 nucleotide sequence (nucleotides 14-2311 of SEQ ID NO: 1) and the human TRPV2 nucleotide sequence (Genbank accession #: AF129112) (SEQ ID NO: 3). The sequences share 86 percent identity. Separately, FIG. 3A illustrates an alignment of the canine TRPV2 nucleotide sequence (nucleotides 1-450 of SEQ ID NO: 1) and the human TRPV2 nucleotide sequence (nucleotides 1-450 of SEQ ID NO: 3), FIG. 3B illustrates an alignment of the canine TRPV2 nucleotide sequence (nucleotides 451-950 of SEQ ID NO: 1) and the human TRPV2 nucleotide sequence (nucleotides 451-947 of SEQ ID NO: 3), FIG. 3C illustrates an alignment of the canine TRPV2 nucleotide sequence (nucleotides 951-1447 of SEQ ID NO: 1) and the human TRPV2 nucleotide sequence (nucleotides 948-1444 of SEQ ID NO: 3), FIG. 3D illustrates an alignment of the canine TRPV2 nucleotide sequence (nucleotides 1448-1947 of SEQ ID NO: 1) and the human TRPV2 nucleotide sequence (nucleotides 1445-1941 of SEQ ID NO: 3), and FIG. 3E illustrates an alignment of the canine TRPV2 nucleotide sequence (nucleotides 1948-2291 of SEQ ID NO: 1) and the human TRPV2 nucleotide sequence (nucleotides 1942-2288 of SEQ ID NO: 3).

FIG. 4 illustrates an alignment of the canine TRPV2 amino acid sequence (SEQ ID NO: 2) and the human TRPV2 amino acid sequence (Genbank accession #: AF129112) (SEQ ID NO: 4). The sequences share 84 percent identity.

FIG. 5 illustrates the percent homology between human, murine, rat and canine TRPV2 nucleotide and amino acid sequences.

DETAILED DESCRIPTION OF THE INVENTION

Figure 6:
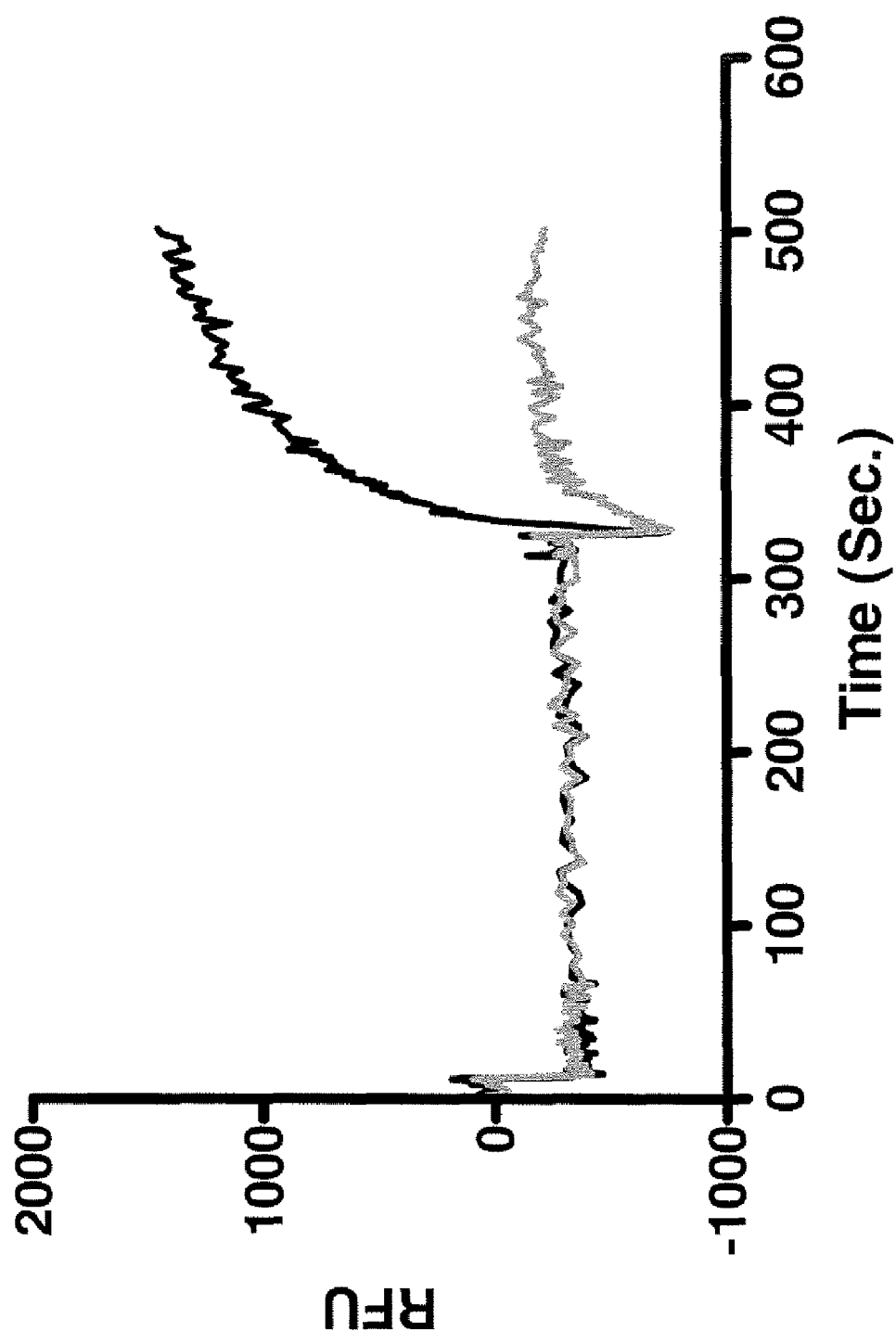
FIG. 6 illustrates the change in cellular calcium levels with addition of 100 μM $\Delta^9$-tetrahydrocannabinol (THC) in HEK293 cells transiently-transfected with canine TRPV2-expressing (black line) or pcDNA3.1 vector control (gray line) plasmid DNA. RFU; Relative Fluorescent Units.

All publications cited herein are hereby incorporated by reference. Unless defined otherwise, all technical and scientific terms used herein have the same meaning as commonly understood to one of ordinary skill in the art to which this invention pertains. As used herein, the terms "comprising", "containing", "having" and "including" are used in their open, non-limiting sense.

"An activity", "a biological activity", or "a functional activity" of a polypeptide or nucleic acid refers to an activity exerted by a polypeptide or nucleic acid molecule as determined in vivo or in vitro, according to standard techniques. Such activities can be a direct activity, such as an association with or an enzymatic activity on a second protein or an ion enzyme activity, or an indirect activity, such as a cellular signaling activity mediated by interaction of the protein with one or more than one additional protein or other molecule(s), including, but not limited to, interactions that occur in a multi-step, serial fashion.

A "biological sample" or "sample" as used herein refers to a sample containing or consisting of cell or tissue matter, such as cells, cell associated body fluids, biological fluids, culture supernatants, DNA, RNA, or protein isolated from a subject or patient. The "subject" can be bacteria, yeast, arthropods, a mammal, such as a rat, a mouse, a canine, a human, or any other organism, that has been the object of treatment, observation or experiment. Examples of biological samples include, for example, saliva, sputum, blood, blood cells (e.g., white blood cells), amniotic fluid, plasma, semen, bone marrow, tissue or fine-needle biopsy samples, urine, peritoneal fluid, pleural fluid, and cell cultures. Biological samples can also include sections of tissues, such as frozen sections taken for histological purposes.

A "cell" refers to at least one cell or a plurality of cells appropriate for the sensitivity of the detection method. Cells suitable for the present invention can be mammalian, for example, canine cells, or other prokaryote cells.

A "clone" is a population of cells derived from a single cell or common ancestor by mitosis. A "cell line" is derived from clonal expansion of primary cells, and is capable of stable growth in vitro for many generations.

A "DNA clone" is a section of DNA that has been copied, isolated or removed from a host and inserted into a vector molecule, such as a plasmid or a phage, or a chromosome, and then replicated to form many identical copies.

The term "cDNA" as used herein means a complementary DNA (cDNA) that has been reverse transcribed from a specific RNA template through the action of the enzyme reverse transcriptase.

A "gene" is a segment of DNA involved in producing a peptide, polypeptide, or protein, and the mRNA encoding such protein species, including the coding region, non-coding regions preceding ("5'UTR") and following ("3'UTR") the coding region. A "gene" can also include intervening non-coding sequences ("introns") between individual coding segments ("exons"). "Promoter" means a regulatory sequence of DNA that is involved in the binding of RNA polymerase to initiate transcription of a gene. Promoters are often upstream of (or 5' to) the transcription initiation site of the gene. A "regulatory sequence" refers to the portion of a gene that can control the expression of the gene. A "regulatory sequence" can include promoters, enhancers and other expression control elements such as polyadenylation signals, ribosome binding site (for bacterial expression), and/or an operator.

"Nucleic acid sequence" or "nucleotide sequence" refers to the arrangement of either deoxyribonucleotide or ribonucleotide residues in a polymer in either single- or double-stranded form. Nucleic acid sequences can be composed of natural nucleotides of the following bases: thymidine, adenine, cytosine, guanine, and uracil; abbreviated T, A, C, G, and U, respectively, and/or synthetic analogs. Synthetic analogs can include nucleotide and nucleoside analogs as well as non-nucleotide and non-nucleoside analogs.

The term "oligonucleotide" refers to a single-stranded DNA or RNA sequence of a relatively short length, for example, less than 100 residues long. For many methods, oligonucleotides of about 15-40 nucleotides in length are useful, although longer oligonucleotides of greater than about 40 nucleotides can sometimes be utilized. Some oligonucleotides can be used as "primers" for the synthesis of complimentary nucleic acid strands. For example, DNA primers can hybridize to a complementary nucleic acid sequence to prime the synthesis of a complementary DNA strand in reactions using DNA polymerases. Oligonucleotides are also useful for hybridization in several methods of nucleic acid detection, for example, in Northern blotting or in situ hybridization.

The term "probe" as used herein refers to a nucleic acid that can selectively hybridize under stringent hybridization conditions to a nucleic acid molecule comprising a nucleotide sequence that encodes a polypeptide capable of TRPV2 activity and having at least 90% sequence identity to SEQ ID NO: 2. Additionally, a probe can selectively hybridize under stringent hybridization conditions to a polypeptide capable of TRPV2 activity and having at least 90% sequence identity to SEQ ID NO: 2. Nucleic acid probes can be of any practical length similar to oligonucleotides in general and can be RNA or DNA, as described above. For example, probes can be from 10-20, 21-40, 41-60, or greater than 61 nucleotides in length. Such probes are useful for the detection of TRPV2 molecules in heterogeneous mixtures or for the amplification of rare copies, genomic copies and recombinant copies in vectors, as in the case of polymerase chain reactions, South-western blots and other common molecular biology techniques. Hybridization conditions are well known in the art, for example, but not limited to, those described in Sambrook et al., Molecular Cloning: A Laboratory Manual, Second Edition, Cold Spring Harbor Laboratory, Cold Spring Harbor, N.Y., (1989).

A "polypeptide sequence" or "protein sequence" refers to the arrangement of amino acid residues in a polymer. Polypeptide sequences can be composed of the standard 20 naturally occurring amino acids, in addition to rare amino acids and synthetic amino acid analogs. Shorter polypeptides are generally referred to as peptides.

An "isolated" or "purified" nucleic acid molecule is one that is substantially separated from other nucleic acid molecules present in the natural source of the nucleic acid. An "isolated" nucleic acid molecule can be, for example, a nucleic acid molecule that is free of at least one of the nucleotide sequences that naturally flank the nucleic acid molecule at its 5' and 3' ends in the genomic DNA of the organism from which the nucleic acid is derived. Isolated nucleic acid molecules include, without limitation, separate nucleic acid molecules (e.g., cDNA or genomic DNA fragments produced by PCR or restriction endonuclease treatment) substantially independent of other sequences, as well as nucleic acid molecules that are incorporated into a vector, an autonomously replicating plasmid, a virus (e.g., a retrovirus, adenovirus, or herpes virus), or into the genomic DNA of a prokaryote or eukaryote. In addition, an isolated nucleic acid molecule can include a nucleic acid molecule that is part of a hybrid or fusion nucleic acid molecule. An isolated nucleic acid molecule can be a nucleic acid molecule that is: (i) amplified in vitro by, for example, polymerase chain reaction (PCR); (ii) synthesized by, for example, chemical synthesis; (iii) recombinantly produced by cloning; or (iv) purified, for example, by cleavage and electrophoretic or chromatographic separation.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium (i.e., culture medium represents less than about 20%, 10%, or 5% of the volume of the protein preparation). When the protein is produced by chemical synthesis, it is preferably substantially free of chemical precursors or other chemicals (i.e., it is separated from chemical precursors or other chemicals that are involved in the synthesis of the protein). Accordingly such preparations of the protein have less than about 30%, 20%, 10%, and 5% (by dry weight) of chemical precursors or compounds other than the polypeptide of interest. Isolated biologically active polypeptides can have several different physical forms. An isolated polypeptide can exist as a full-length nascent or unprocessed polypeptide, or as a partially processed polypeptide or as a combination of processed polypeptides. The full-length nascent polypeptide can be posttranslationally modified by specific proteolytic cleavage events that result in the formation of fragments of the full-length nascent polypeptide. The full-length protein or fragments of the polypeptide can be chemically modified. A fragment, or physical association of fragments can have the biological activity associated with the full-length polypeptide; however, the degree of biological activity associated with individual fragments can vary. An isolated or substantially purified polypeptide, can be a polypeptide encoded by an isolated nucleic acid sequence as well as a polypeptide synthesized by, for example, chemical synthetic methods, and a polypeptide separated from biological materials, and then purified, using conventional protein analytical or preparatory procedures, to an extent that permits it to be used according to the methods described herein.

The terms "reducing expression", "decreasing expression", "knocking down" and "knock down" as used herein to refer to the reduction in the expression of one or more than one gene. This reduction in gene expression can be as a result of a reduction in the rates of transcription or translation or an increase in the rates of degradation or any combination of the above. For example, TRPV2 gene expression can be reduced through the use of RNA interference technology. Suitable RNA interference techniques are described and reviewed by Sandy et. al in Biotechniques. 2005 August; 39(2): 215-24, Mammalian RNAi: a Practical Guide, which is incorporated by reference.

The term "antisense" as used herein refers to a noncoding molecule that is complementary to the bases of a coding sequence of mRNA. Introducing a transgene coding for antisense mRNA is another strategy used to reduce or knock down expression of a gene. A strand of antisense mRNA can also be introduced into the cytosol by microinjection.

Analogous molecules with modified backbones have been designed, which change various characteristics of RNA, such as its instability to degradative enzymes, thermal stability and bond strength, thereby altering gene expression. Some alternative antisense structural types include phosphorothioate, PNA (peptide nucleic acid), LNA (locked nucleic acid), and 2'-O alkyl oligos.

The term "selectively hybridize" as used herein refers to the ability of a probe to bind to a particular or intended nucleic acid or polypeptide target sequence or molecule in a heterogeneous mixture of nucleic acids or polypeptides, for example, a probe can selectively hybridize to a nucleotide sequence encoding a TRPV2 or a polypeptide capable of TRPV2 activity in a heterogeneous mixture.

"Recombinant" refers to a nucleic acid, a protein encoded by a nucleic acid, a cell, or a viral particle, that has been modified using molecular biology techniques to something other than its natural state. For example, recombinant cells can contain nucleotide sequence that is not found within the native (non-recombinant) form of the cell or can express native genes that are otherwise abnormally expressed, under-expressed, or not expressed at all. Recombinant cells can also contain genes found in the native form of the cell wherein the genes are modified and re-introduced into the cell by artificial means. The term also encompasses cells that contain an endogenous nucleic acid molecule that has been modified without removing the nucleic acid from the cell; such modifications include those obtained, for example, by gene replacement and site-specific mutation.

A "recombinant host cell" is a cell that has had introduced into it a recombinant DNA sequence. Recombinant DNA sequences can be introduced into host cells using any suitable method, including, for example, electroporation, calcium phosphate precipitation, microinjection, transformation, biolistics "gene-gun" and viral infection. Recombinant DNA may or may not be integrated (covalently linked) into chromosomal DNA making up the genome of the cell. For example, the recombinant DNA can be maintained on an episomal element, such as a plasmid. Alternatively, with respect to a stably transformed or transfected cell, the recombinant DNA has become integrated into the chromosome so that it is inherited by daughter cells through chromosome replication. This stability is demonstrated by the ability of the stably transformed or transfected cell to establish cell lines or clones comprised of a population of daughter cells containing the exogenous DNA. Recombinant host cells can be prokaryotic or eukaryotic, including, E. coli, fungal cells, such as yeast, mammalian cells, such as cell lines of human, bovine, porcine, canine and rodent origin, and insect cells, such as Drosophila- and silkworm-derived cell lines. It is further understood that the term "recombinant host cell" refers not only to the particular subject cell but also to the progeny or potential progeny of such a cell. Because certain modifications can occur in succeeding generations, due to either mutation or environmental influences, such progeny cannot, in fact, be identical to the parent cell but are still included within the scope of the term as used herein.

The term "vector" or "construct" refers to a nucleic acid molecule into which a heterologous nucleic acid can be or is inserted. Some vectors can be introduced into a host cell allowing for replication of the vector or for expression of a protein that is encoded by the vector or construct. Vectors typically have selectable markers, for example, genes that encode proteins allowing for drug resistance, origins of replication sequences, and multiple cloning sites that allow for insertion of a heterologous sequence. Vectors are typically plasmid-based and are designated by a lower case "p" followed by a combination of letters and/or numbers. Starting plasmids disclosed herein are either commercially available, publicly available on an unrestricted basis, or can be constructed from available plasmids by application of procedures known in the art. Many plasmids and other cloning and expression vectors that can be used in accordance with the present invention are well known and readily available to those of skill in the art. Moreover, those of skill readily can construct any number of other plasmids suitable for use in the invention. The properties, construction and use of such plasmids, as well as other vectors, in the present invention will be readily apparent to those of skill from the present disclosure.

The term "expression" as used herein refers to a multi-step process that includes transcription and translation of a gene and is often followed by post-translational modification, folding, assembly and trafficking/targeting of the resulting protein. The amount of protein that a cell expresses depends on the tissue, the developmental stage of the organism and the metabolic or physiologic state of the cell.

The term "expression vector" refers to a vector that comprises regulatory sequences necessary for transcription and translation of a cloned gene or genes and thus can transcribe and clone DNA. An expression vector can include one or more than one regulatory sequence, which can be selected based on the type of host cells used, operably linked to a gene. Regulatory sequences include promoters, enhancers and other expression control elements, for example, poly (A)+ sequences. Other expression vector components can include, but are not limited to, one or more than one of the following: a signal sequence, an origin of replication, one or more than one selection gene and a transcription termination sequence.

"Sequence" means the linear order in which monomers occur in a polymer, for example, the order of amino acids in a polypeptide or the order of nucleotides in a polynucleotide.

"Sequence identity or similarity", as known in the art, is the relationship between two or more polypeptide sequences or two or more polynucleotide sequences, as determined by comparing the sequences. As used herein, "identity", in the context of the relationship between two or more nucleic acid sequences or two or more polypeptide sequences, refers to the percentage of nucleotide or amino acid residues, respectively, that are the same when the sequences are optimally aligned and analyzed. For the purposes of comparing a queried sequence against, for example, the amino acid sequence SEQ ID NO: 2, the queried sequence is optimally aligned with SEQ ID NO: 2 and the best local alignment over the entire length of SEQ ID NO: 2 (331 amino acids) is obtained.

Analysis can be carried out manually or using sequence comparison algorithms. For sequence comparison, typically one sequence acts as a reference sequence, to which a queried sequence is compared. When using a sequence comparison algorithm, test and reference sequences are input into a computer, sub-sequence coordinates are designated, if necessary, and sequence algorithm program parameters are designated.

Optimal alignment of sequences for comparison can be conducted, for example, by using the homology alignment algorithm of Needleman & Wunsch, J. Mol. Biol., 48:443 (1970). Software for performing Needleman & Wunsch analyses is publicly available through the Institut Pasteur (France) Biological Software website. The NEEDLE program uses the Needleman-Wunsch global alignment algorithm to find the optimum alignment (including gaps) of two sequences when considering their entire length. The identity is calculated along with the percentage of identical matches between the two sequences over the reported aligned region, including any gaps in the length. Similarity scores are also provided wherein the similarity is calculated as the percentage of matches between the two sequences over the reported aligned region, including any gaps in the length. Standard comparisons utilize the EBLOSUM62 matrix for protein sequences and the EDNAFULL matrix for nucleotide sequences. The gap open penalty is the score taken away when a gap is created; the default setting using the gap open penalty is 10.0. For gap extension, a penalty is added to the standard gap penalty for each base or residue in the gap; the default setting is 0.5.

Hybridization can also be used as a test to indicate that two polynucleotides are substantially identical to each other. Polynucleotides that share a high degree of identity will hybridize to each other under stringent hybridization conditions. "Stringent hybridization conditions" has the meaning known in the art, as described in Sambrook et al., Molecular Cloning: A Laboratory Manual, Second Edition, Cold Spring Harbor Laboratory, Cold Spring Harbor, N.Y., (1989). An exemplary stringent hybridization condition for an oligonucleotide probe comprises hybridization in 6× sodium chloride/sodium citrate (SSC) at about 45° C., followed by one or more than one wash in 0.2×SSC and 0.1% SDS at 50-65° C., depending upon the length over which the hybridizing polynucleotides share complementarity.

A "reporter gene" refers to a nucleic acid sequence that encodes a reporter gene product. As is known in the art, reporter gene products are typically easily detectable by standard methods. Exemplary suitable reporter genes include, but are not limited to, genes encoding luciferase (lux), β-galactosidase (lacZ), green fluorescent protein (GFP), chloramphenicol acetyltransferase (CAT), β-glucuronidase, neomycin phosphotransferase, and guanine xanthine phosphoribosyl-transferase proteins.

The term "marker" as used herein refers to a specific substance from a subject that has a particular molecular feature that makes it useful for measuring the progress of disease or the effects of treatment. Biological samples comprising the marker are taken at periodic intervals from the subject to measure the progress of disease or the effects of treatment. The first measure of the marker is compared to the second measure and/or subsequent measures. In another example, the measure of the marker can be compared to a reference, a standard or a negative control.

TRPV's are vanilloid sub-family members of the 6 transmembrane domain transient receptor potential (TRP) superfamily. Structural, biochemical and pharmacological analyses of the TRPV genes and proteins has led to the discovery of 6 distinct members, including TRPV1 and TRPV2, which are thermo-sensitive to noxious heat. Activation of TRPV's mediates several receptor subtype-specific physiological processes that include but are not limited to the regulation of cellular calcium levels, excitability and transmitter release as well as sensory transduction and homeostasis.

The term "TRPV2 channel," as used herein includes any receptor that can be naturally occurring, cloned, mutated, recombinantly expressed, chemically modified or substituted with amino acid analogs while maintaining TRPV channel activity.

The term "epitope" as used herein refers to a site on a large molecule against which an antibody may be produced and to which it will bind. Epitopes can be naturally occurring or chemically or synthetically produced.

A "compound that decreases the activity of TRPV2 channel" includes any compound that results in decreased signaling through the TRPV2 channel. In one embodiment, such a compound can be a partial agonist. In another embodiment, such a compound can be an antagonist, which can be either competitive or non-competitive. In another embodiment the compound can be both a partial agonist and an antagonist.

A "compound that increases the activity of TRPV2 receptor" includes any compound that results in increased signaling through the TRPV2 channel. Such a compound can be an agonist or a partial agonist.

A kit is any manufacture (e.g., a package or container) comprising at least one reagent, the manufacture being promoted, distributed, or sold as a unit for performing the methods of the present invention.

A putative homolog of TRPV2 from canine (SEQ ID NO: 1) has now been cloned. The TRPV2 of canine provides a means for identification of TRPV2 antagonists and agonists with potential utility for treating certain types of pain and painful conditions, including but not limited to neuropathic pain and inflammatory pain. An alignment of the canine TRPV2 nucleotide sequence and the human TRPV2 nucleotide sequence is shown in FIGS. 3A-3E. FIGS. 3A-3E show an 86 percent sequence identity between these two sequences. An alignment of the canine TRPV2 amino acid sequence and the human TRPV2 amino acid sequence is shown in FIG. 4. FIG. 4 shows an 84 percent sequence identity between these two sequences.

The present invention relates to novel TRPV2 nucleic acids, polypeptides and proteins encoded by these nucleic acids, recombinant TRPV2 materials, and methods involving the production, detection, and utilization of these materials.

Inhibition of the function or expression of TRPV2 proteins can be advantageous for screening and validating drug candidates both in vitro and in vivo. Since TRPV2 is implicated in noxious heat sensation, it is anticipated that inhibition of TRPV2 activity is also relevant for therapeutic applications where neuropathic, inflammatory and chronic pains occur.

In attempts to clone the TRPV2 orthologous, a PCR-based strategy was employed. Oligonucleotide primers were synthesized according to the sequences set forth in SEQ ID NO: 5 and SEQ ID NO: 6. These primers were successfully used to amplify a portion of the TRPV2 sequence from position 761 to position 2200 SEQ ID NO: 1. The full length cDNA was then cloned by both 5' and 3' RACE-PCR. In the present invention, the TRPV2 gene was cloned from the cDNA of canine dorsal root ganglion. The TRPV2 gene was sequenced, and the nucleotide sequence is shown as SEQ ID NO: 1 (see also, FIGS. 1A-1C). SEQ ID NO: 1 encodes a 765 residue polypeptide (see, SEQ ID NO:2), as shown in FIG. 2.

In the present invention, the TRPV2 nucleic acid was also subcloned into an expression vector and transformed into a host cell for expression of the TRPV2 protein. This recombinant TRPV2 cell system was shown to express a functional TRPV2 protein that responded to $\Delta^9$-THC in a dose-dependent manner.

In other diagnostic assays which are capable of detecting the expression of TRPV2, the level of expression of mRNA corresponding to the TRPV2 gene can be detected utilizing commonly used molecular biological methods, for example, Northern blotting, in situ hybridization, nuclease protection assays, RT-PCR (including real-time, quantitative PCR), high density arrays and other hybridization methods. Accordingly, in another embodiment, an assay capable of detecting the expression of one or more than one TRPV2 gene in a biological sample is provided, which comprises contacting a biological sample with an oligonucleotide capable of hybridizing to a TRPV2 nucleic acid. The oligonucleotide is generally from 10-20 nucleotides in length for PCR/primer extension experiments. Longer oligonucleotides of approximately 40-50 nucleotides are more regularly utilized for in situ or blot hybridizations. Sequences even longer than 50 nucleotides can also be employed in the detection methods of this invention. RNA can be isolated from the tissue sample by methods well-known to those skilled in the art as described, for example, in Ausubel et al., Current Protocols in Molecular Biology, John Wiley and Sons, Inc. (1996). One preferred method for detecting the level of mRNA transcribed from the TRPV2 genes is by RT-PCR. Details of RT-PCR techniques are well known and also described, for example, in Pfeffer et al. Efficient one-tube RT-PCR amplification of rare transcripts using short sequence-specific reverse transcription primers. BioTechniques 18, 204-206. (1995) and Giannoni et al. An improved reverse transcription-polymerase chain reaction method to study a lipoprotein gene. Journal of Lipid Research 35 (2): 340 (1994).

Optionally, all or a portion of the TRPV2 nucleic acid sequence can be used to probe nucleic acid preparations from other species to determine the presence of similar sequences. For example, all or a portion of the TRPV2 nucleic acid can be used as a probe to identify cDNA or genomic nucleic acid sequences from other species that are similar to the TRPV2 sequence. Positive clones can be identified as those that hybridize to the TRPV2 probe.

The invention also relates to isolated nucleic acid fragments. Isolated nucleic acids comprising fragments of SEQ ID NO: 1 are useful for a variety of purposes. For example, these sequences can be used as oligonucleotide probes for the detection of TRPV2 nucleic acids or for the detection of sequences that flank TRPV2 nucleic acids. These sequences can be used as oligonucleotide primers for the amplification of TRPV2 nucleic acids. For many methods, oligonucleotides of about 16-25 nucleotides, or from about 26-35 nucleotides in length are useful, although longer oligonucleotides of greater than about 35 nucleotides can also be utilized. Some oligonucleotides can be used as "primers" for the synthesis of complimentary nucleic acid strands. For example, DNA oligonucleotide primers can hybridize to a complimentary nucleic acid sequence to prime the synthesis of a complimentary DNA strand in reactions using DNA polymerases. Oligonucleotides are also useful for hybridization in several methods of nucleic acid detection, for example, in Northern blotting or in situ hybridization. Fluorescently-labeled oligonucleotides, for example, Cy3-dCTP-labeled fluorescent cDNA probes, are particularly useful in hybridization methods using microarrays. Oligonucleotides can also be used for the preparation of chimeric nucleic acids that encode a portion or all of the TRPV2 polypeptide fused to another polypeptide sequence, for example, one or more than one motif or domain of the TRPV2 sequence recombined with one or more than one motif or domain from one or more than one heterologous sequence. In some embodiments, this can affect the activity of the TRPV2 channel. Oligonucleotides can be used in other methods; for example, RT-PCR using SEQ ID: 5 and SEQ ID: 6 or SEQ ID: 7 and SEQ ID: 8 can be used to identify TRPV2 expression. Oligonucleotides can further be used in techniques such as RNAi to reduce TRPV2 expression. In addition to nucleic acid sequences encoding TRPV2 polypeptides, the invention also includes TRPV2 polypeptides, TRPV2 polypeptide variants, fragments of TRPV2 polypeptides and TRPV2 polypeptides having additional amino acids.

TRPV2 polypeptide variants are polypeptides capable of TRPV2 activity in which substitutions have been made in the amino acid sequence from the sequence shown in SEQ ID NO: 2. These substitutions can be as a result of naturally occurring mutations during DNA synthesis, transcription or translation, the use of amino acid analogs, chemical modifications or other molecular biology techniques well known in the art.

Fragments of TRPV2 polypeptides include polypeptides capable of TRPV2 activity, which are shorter in length than the sequence shown in SEQ ID NO: 2. These fragments include any polypeptide capable of TRPV2 activity, which are less than around 95 amino acids in length. For example, a fragment of TRPV2 can be from 65 to about 735 amino acids in length and still be capable of TRPV2 activity. Fragments of TRPV2 polypeptides may be created by naturally occurring mutations during DNA synthesis, transcription or translation. Those skilled in the art will readily recognize that the use of enzymes that cleave either DNA or proteins, chemical modifications or other molecular biology techniques can be employed to create fragments of TRPV2 polypeptides.

TRPV2 polypeptides or TRPV2 polypeptide fragments can be generated using any sort of synthetic or molecular biological technique. Standard synthetic peptide techniques can be used to generate smaller TRPV2 polypeptide fragments. Techniques for the synthesis of peptide fragments are well known and are described in, for example, Barany and Merrifield, Solid-Phase Peptide Synthesis; pp. 3-284 in The Peptides: Analysis, Synthesis, Biology. Vol. 2: Special Methods in Peptide Synthesis, Part A., Merrifield, et al., J. Am. Chem. Soc., 85: 2149-2156 (1963), and Stewart et al., Solid Phase Peptide Synthesis, 2nd ed. Pierce Chem. Co., Rockford, Ill. (1984).

TRPV2 polypeptides that have additional amino acids and are longer in length than the sequence shown in SEQ ID NO: 2 are also envisioned within the scope of the invention. As described herein, the TRPV2 polypeptide can also have additional amino acid residues at its amino terminus, its carboxyl terminus or both. Such additional residues are useful for a variety or purposes, including, for example, immunodetection, purification, cellular trafficking, enzymatic activity, etc. These proteins can include any polypeptide capable of TRPV2 activity, which is greater than 10 amino acids in length. For example a recombinant TRPV2 can be from 1 to about 775 amino acids in length and still be capable of TRPV2 activity. Recombinant TRPV2 polypeptides can be created by naturally occurring mutations during DNA synthesis, transcription or translation, the use of enzymes that either ligate DNA, such as T4 ligase, or fuse proteins.

Additionally fragments of TRPV2 and TRPV2 polypeptides having additional amino acids can comprise variant sequences in which substitutions have been made in the amino acid sequence from the sequence shown in SEQ ID NO: 2. These substitutions can be as a result of naturally occurring mutations during DNA synthesis, transcription or translation, the use of amino acid analogs, chemical modifications or other molecular biology techniques well known in the art.

A nucleic acid sequence can encode a TRPV2 fusion protein, which can include additional amino acid residues providing coordinates for bonding, such as ionic, covalent, hydrogen or Van der Waals or combinations thereof with organic or inorganic compounds. Useful additional amino acid sequences include, for example, poly-histidine residues useful for protein purification via Ni+-coupled residue, constant domains of immunoglobulins (IgA, IgE, IgG, IgM) or portions thereof (CH1, CH2, CH3), albumin, hemagluttinin (HA) or myc affinity epitope tags useful for the formation of immuno-complexes for detection or purification (antibodies against these moieties can be obtained commercially), polypeptides useful for detection such as the green fluorescent protein (GFP), enzymes, such as beta-galactosidase (β-Gal), glutathione S-transferase (GST), chloramphenicol acetyltransferase (CAT), luciferase, and alkaline phosphatase (A), signal sequences for protein trafficking and protease cleavage sequences useful for separating additional amino acid sequences from the TRPV2 sequence, if desired. Those skilled in the art will readily recognize that chemical modifications or other molecular biology techniques can be employed to create recombinant proteins or protein fusions. Fragments of TRPV2 and TRPV2 polypeptides having additional amino acids can comprise variant sequences in which substitutions have been made in the amino acid sequence as compared with the sequence shown in SEQ ID NO: 2. These substitutions can be as a result of naturally occurring mutations during DNA synthesis, transcription or translation, the use of amino acid analogs, other molecular biology techniques, or chemical modifications well known in the art.

Due to the degeneracy of the genetic code, more than one codon can be used to encode a particular amino acid, and therefore, a TRPV2 amino acid sequence (for example, SEQ ID NO: 2) can be encoded by any one of a plurality of nucleic acid sequences. Isolated nucleic acid includes sequences wherein one or more than one codon in the sequence is replaced by one or more than one codon of a different sequence but that encodes the same amino acid residue are herein referred to as "conservative codon substitutions". Therefore, the invention encompasses nucleic acid sequences encoding SEQ ID NO: 2, which have one or more than one conservative codon substitution. One of skill in the art would be able to determine a particular nucleic acid sequence having one or more than one conservative codon substitution and encoding SEQ ID NO: 2, based on the sequence information provided herein. Conservative codon substitutions can be made in the nucleic acid sequence encoding the TRPV2 polypeptide, for example, the codons TTT and TTC (collectively referred to as TTT/C) can encode a Phe (phenylalanine) residue; other codon substitutions are as follows: TTA/G and CTT/C/A/G: Leu; ATT/C: Ile; ATG: Met; GTT/C/A/G: Val; TCT/C/A/G: Ser; CCT/C/A/G: Pro; ACT/C/A/G: Thr; GCT/C/A/G: Ala; TAT/C: Tyr; CAT/C: His; CAA/G: Gln; AAT/C: Asn; AAA/G: Lys; GAT/C: Asp; GAA/G Glu; TGT/C: Cys; GT/C/A/G: Arg; AGT/C: Ser; AGA/G; Arg; GGT/C/A/G: Gly. Conservative codon substitutions can be made at any position in the nucleic acid sequence that encodes the TRPV2 polypeptide.

The isolated nucleic acids of the invention can also include nucleic acid sequences that encode the TRPV2 polypeptide having additional amino acid residues. In some embodiments, the additional amino acids are present at the amino terminus, the carboxyl terminus, within the TRPV2 sequence or combinations of these locations. TRPV2 polypeptides having these types of additional amino acid sequences can be referred to as "TRPV2 fusion proteins". In some cases, it may be more appropriate to refer to them otherwise as "chimeric" or "tagged" TRPV2 proteins, or the like, depending on the nature of the additional amino acid sequences. Nonetheless, one will be able to discern a TRPV2 polypeptide having additional amino acid sequences given the sequence information provided herein. The additional amino acid residues can be few in number, for example, from one to about 20 additional amino acid residues, or longer, for example, greater than about 20 additional amino acid residues. The additional amino acid residues can serve one or more than one function or purpose including, for example, serving as epitopes for protein (e.g., antibody) or small molecule binding; serving as tags for intracellular and extracellular trafficking; providing additional enzymatic or other activity; or providing a detectable signal.

Recombinant techniques can be used for the expression of TRPV2 including but not limited to fragments of TRPV2, variants of TRPV2 and fusions of TRPV2 with other proteins from host cells transformed with a TRPV2 nucleic acid. These methods include, for example, in vitro recombinant DNA techniques and in vivo genetic recombination (for example, see the techniques described in Sambrook et al., Molecular Cloning, A Laboratory Manual, 3rd Edition, Cold Spring Harbor Press, NY (2001); and Ausubel et al., eds., Short Protocols in Molecular Biology, 4th Edition, John Wiley & Sons, Inc., NY (1999)).

TRPV2 can be produced by introducing an expression vector encoding a TRPV2 polypeptide into a cell and culturing the cells to express the polypeptide. When a purified TRPV2 polypeptide is desired, a step can also be performed to isolate and, if desired, purify the TRPV2 polypeptide.

In another embodiment, the invention provides a recombinant nucleic acid construct that includes all or a portion of the TRPV2 coding sequence operably linked to a regulatory sequence. These recombinant nucleic acid constructs include recombinant expression vectors suitable for expression of the TRPV2 nucleic acid in a host cell. Recombinant expression vectors include one or more than one regulatory sequence that can be selected based on the type of host cells used for TRPV2 expression, operably linked to a TRPV2 nucleic acid sequence. Regulatory sequences include promoters, enhancers and other expression control elements, for example, poly (A)+ sequences. Regulatory sequences can be specific for prokaryotic cells, for example, bacterial cells, such as E. coli, or for eukaryotic cells, such as yeast cells, insect cells or mammalian cells (for example, HEK, CHO or COS cells). Regulatory sequences can be located cis or trans relative to the TRPV2 nucleic acid sequence. Regulatory sequences can include constitutive expression sequences that typically drive expression of the nucleic acid under a wide variety of growth conditions and in a wide variety of host cells, tissue-specific regulatory sequences that drive expression in particular host cells or tissues and inducible regulatory sequences that drive expression in response to a secondary factor. The choice and design of the expression vector can depend on such factors as the particular host cell utilized and the desired levels of polypeptide expression. Genes facilitating selection of transformed cells encode proteins that confer resistance to antibiotics or other toxins, for example, ampicillin, neomycin, methotrexate or tetracycline, complement auxotrophic deficiencies or supply critical nutrients not available from complex media.

Recombinant nucleic acid constructs used for expression of the TRPV2 polypeptide can also include constructs that can be transcribed and translated in vitro, for example, constructs having a T7 promoter regulatory sequence.

Vectors suitable for the expression of TRPV2 are known in the art and commercially available. Suitable vectors include, for example, pcDNA3.1, pCI-neo, pET-14b, pcDNAl Amp and pVL1392, which are available from Novagen and Invitrogen and can be used for expression in E. coli, COS cells and baculovirus infected insect cells, respectively.

In another embodiment, the invention provides a recombinant cell that includes a TRPV2 nucleic acid. Recombinant cells include those wherein a nucleic acid sequence has been introduced. Typically, recombinant cells are created by introducing a particular nucleic acid into cells using molecular biological techniques. However, recombinant cells also include cells that have been manipulated in other ways to promote the expression of a desired nucleic acid sequence. For example, regions that are proximal to a target nucleic acid sequence can be altered to promote expression of the target nucleic acid, or genes that act to regulate the expression of a target nucleic acid can be introduced into a cell. Recombinant cells, after periods of growth and division, may not be identical to the starting parent cell; however, these cells are still referred to as recombinant cells and are included within the scope of the term as used herein.

Host cells suitable for harboring and providing the machinery for TRPV2 expression include any prokaryotic or eukaryotic cells. Examples of suitable prokaryotic host cells are eubacteria, such as gram-negative or gram-positive organisms, for example, Enterobacteriaceae such as *Escherichia*, for example, *E. coli, Enterobacter, Salmonella*, for example, *Salmonella typhimurium*, as well as Bacilli, such as *B. subtilis, Pseudomonas*, and *Streptomyces*. Many higher eukaryotic host cells can be used, including insect cells, such as *Drosophila* S2 and *Spodoptera* Sf9 cells, mammalian cells, such as U937, THP-1, Chinese Hamster Ovary (CHO) cells, canine kidney (COS) cells, canine kidney (MDCK) cells, human cervical carcinoma (HeLa) cells, and human embryonic kidney (HEK) cells as well as plant cells.

Growth of the transformed host cells can occur under conditions that are known in the art. The conditions will generally depend upon the host cell and the type of vector used. Suitable induction conditions, such as temperature and chemicals, can be used and will depend on the type of promoter utilized. Examples of suitable media for the propagation of prokaryotes include Luria Broth (LB), also known as Miller's L Broth. Examples of suitable media for the propagation of eukaryotes include, Minimal Essential Medium (MEM), RPMI-1640, Dulbecco's Modified Eagle's Medium (DMEM) and F12 Medium.

Nucleic acids, including expression constructs, can be introduced into prokaryotic or eukaryotic cells via conventional transformation or transfection techniques. As used herein, the terms "transformation" and "transfection" are intended to refer to a variety of art-recognized techniques for introducing a foreign nucleic acid molecule (e.g., DNA) into a host cell, including calcium phosphate or calcium chloride co-precipitation, DEAE-dextran-mediated transfection, lipofection, virus mediated introduction, biolistics or electroporation. Suitable methods for transforming or transfecting host cells can be found in Sambrook, et al. (supra) and other laboratory manuals.

Recombinant cells can be useful for the production of a TRPV2 polypeptide for purification purposes or for functional studies involving the TRPV2 polypeptide. For example, a recombinant TRPV2 cell can be used to test a number of compounds for their ability to alter the activity of the TRPV2 polypeptide. The recombinant TRPV2 cell can also be used to test how altering various properties of the TRPV2 polypeptide, for example, altering the amino acid sequence of the TRPV2 polypeptide, affects TRPV2 activity.

A variety of methods can be used for purification of the TRPV2 polypeptide. For example, crude purification can be performed using ammonium sulfate precipitation, centrifugation or other known techniques. A higher degree of purification can be achieved by suitable chromatographic techniques, including, for example, anion exchange, cation exchange, high performance liquid chromatography (HPLC), gel filtration, hydrophobic interaction chromatography and affinity chromatography, for example, immunoaffinity chromatography using antibodies directed against the TRPV2 protein. If needed, steps for refolding the TRPV2 proteins can be used to obtain the active conformation of the protein when the protein is denatured during intracellular synthesis, isolation or purification, such as resuspending the protein in 6M urea and dialyzing out the urea to facilitate protein refolding.

The invention also provides novel antibodies that selectively bind to the proteins of the present invention as well as fragments thereof. Such antibodies can be used to quantitatively or qualitatively detect the protein or peptide molecules of the present invention. As used herein, an antibody selectively binds a target protein or polypeptide fragment when an antibody binds the protein or polypeptide fragment and does not significantly bind to non-target proteins (i.e., the antibody does not bind non-TRPV2 related polypeptides or proteins).

As used herein, an antibody is defined in terms consistent with that recognized within the art: antibodies are multi-subunit proteins produced by any vertebrate organism in response to an antigen challenge. The antibodies of the present invention include monoclonal antibodies and polyclonal antibodies, as well as fragments of such antibodies, including, but not limited to, Fab or F(ab')hd 2, Fc, and Fv fragments. Many methods are known for generating and/or identifying antibodies to a given target peptide. Several such methods are described by Harlow, Antibodies, Cold Spring Harbor Press, (1989). In general, to generate antibodies, an isolated peptide is used as an immunogen and is administered to a mammalian organism, such as a rat, rabbit or mouse. Either the full-length protein, an antigenic peptide fragment, or a fusion protein can be used.

Monoclonal antibodies can be produced by hybridomas, which are immortalized cell lines capable of secreting a specific monoclonal antibody. The immortalized cell lines can be created in vitro by fusing two different cell types, usually lymphocytes, one of which is a tumor cell.

Monoclonal antibodies can be obtained by any technique that provides for the production of antibody molecules by continuous cell lines in culture. These include, for example, the hybridoma technique (Kohler and Milstein, Nature, 256: 495-497, 1975); the human B-cell hybridoma technique (Kosbor et al., Immunology Today, 4:72, 1983); and the EBV-hybridoma technique (Cole et al., Monoclonal Antibodies and Cancer Therapy, Alan R. Liss, Inc., pp. 77-96, 1985). Such antibodies can be of any immunoglobulin class, including IgG, IgM, IgE, IgA, IgD or any subclass thereof. The hybridoma producing the monoclonal antibody of this invention can be cultivated in vitro or in vivo.

Antibodies can be prepared from regions or discrete fragments of the protein containing the desired amino acid sequence. Antibodies can be prepared from any region of the peptide as described herein. However, regions that include those involved in function/activity and/or protein/binding partner interaction are preferred. An antigenic fragment will typically comprise at least 10 contiguous amino acid residues. The antigenic peptide can comprise, however, at least 12, 14, 20 or more amino acid residues. Such fragments can be selected on a physical property, such as fragments corresponding to regions that are located on the surface of the protein (e.g., hydrophilic regions) or can be selected based on sequence uniqueness or based on the position of particular amino acid residue(s) or amino acid residue variants of the polypeptides provided by the present invention.

Detection of an antibody of the present invention can be facilitated by coupling (i.e., physically linking) the antibody to a detectable substance. Examples of detectable substances include various enzymes, fluorescent materials, luminescent materials, bioluminescent materials, and radioactive materials. Examples of suitable enzymes include horseradish peroxidase, alkaline phosphatase, $\beta$-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin, and examples of suitable radioactive material include 125 I, 131 I, 35 D or 3 H.

Immunoprecipitation of Ab2 using the antibodies of the present invention for detection of proteins interacting with TRPV2 is also envisioned within the scope of the present invention. Immunoprecipitation can also be used, for example, to discover new disease targets. The TRPV2 antibody can be linked to any immobilizing surface, such as Protein G-sepharose or Protein A-sepharose for the purpose of TRPV2 purification, to identify interacting proteins and potential drug targets. Additionally, the process can be used to determine the molecular weight and isoelectric point of immunoprecipitated proteins by one-dimensional or two-dimensional SDS-PAGE or LC MS/MS. Immunoprecipitation can be used to verify that an antigen of interest is synthesized by a specific tissue (i.e., that a labeled protein can be identified in tissues or cells cultured with labeled precursors). This procedure can be used to determine whether a protein contains carbohydrate residues by evaluating whether immunoprecipitated antigen from cells cultured with labeled monosaccharides is labeled. Characterization of the type of covalent modification, such as phosphorylation or glycosylation wherein the carbohydrates present on glycoproteins, can be performed by evaluating the incorporation of different labeled monosaccharides into immunoprecipitated proteins during cell culture and testing whether inhibitors of glycosylation alter the molecular weight of the immunoprecipitated protein. Immunoprecipitation can be used to determine precursor-product relationships by performing pulse-chase labeling followed by immunoprecipitation. Immunoprecipitation can be used to quantify synthesis rates of proteins in culture by determining the quantity of immunoprecipitated, labeled protein. Methods and reagents for immunoprecipitation are well known in the art and can be obtained from eBioscience, San Diego, Calif. or Upstate USA, Inc. Charlottesville, Va. The invention includes, antibodies useful for immunohistochemistry (IHC) and western blotting applications, for example, human TRPV2-specific antibodies against different regions within the canine TRPV2 protein.

In practicing the present invention, many conventional techniques in molecular biology, microbiology and recombinant DNA are used. These techniques are well-known and are explained in, for example, Current Protocols in Molecular Biology, Vols. I, II, and III, F. M. Ausubel, ed. (1997); and Sambrook et al., Molecular Cloning: A Laboratory Manual, Cold Spring Harbor Laboratory Press, Cold Spring Harbor, N.Y. (2001). The compositions, kits, and methods of the invention have the following uses, among others: 1) selecting a composition or therapy for inhibiting, modulating, or activating TRPV2 in a patient; 2) assessing the efficacy of one or more than one test compound for inhibiting, modulating, or activating TRPV2 in a patient; 3) assessing the efficacy of a therapy for inhibiting, modulating, or activating TRPV2 in a patient; 4) treating a patient afflicted with certain types of pain or painful conditions, including but not limited to neuropathic pain and inflammatory pain.

These types of compounds can be identified using a system that includes a TRPV2 polypeptide or a TRPV2 nucleic acid. Compounds can be tested directly in vivo, for example, in a rat, mouse, canine, or in model systems thereof or directly in bacterial cultures or in eukaryotic cell cultures. These methods comprise assaying for the ability of various compounds to increase or decrease the expression of the TRPV2 protein or the activity of the TRPV2 protein as shown in Example 1. The compound screening and identification methods can be performed using conventional laboratory formats or in assays adapted for high throughput.

Candidate compounds encompass numerous chemical classes, including but not limited to, small organic or inorganic compounds, natural or synthetic molecules, such as antibodies, proteins or fragments thereof, antisense nucleotides, interfering RNA (iRNA) and ribozymes. Preferably, the candidate compounds are small organic compounds (i.e., those having a molecular weight of more than 100 Daltons yet less than about 1000 Daltons). Candidate compounds comprise functional chemical groups necessary for structural interactions with polypeptides and can include at least an amine, carbonyl, hydroxyl or carboxyl group, two of the functional chemical groups or three or more of the functional chemical groups. The candidate compounds can comprise cyclic carbon or heterocyclic structure and/or aromatic or polyaromatic structures substituted with one of the above identified functional groups. Candidate compounds also can be biomolecules, such as peptides, saccharides, fatty acids, sterols, isoprenoids, purines, pyrimidines, derivatives or structural analogs of the above or combinations thereof and the like. Where the compound is a nucleic acid, the compound typically is a DNA or RNA molecule, although modified nucleic acids having non-natural bonds or subunits are also contemplated. Modified nucleic acids can comprise nucleoside analogs, nucleotide analogs, non-nucleoside analogs, non-nucleotide analogs and others.

Candidate compounds are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides and the like. Candidate compounds can also be obtained using any of the numerous approaches in combinatorial library methods known in the art, including biological library methods; spatially addressable, parallel solid phase or solution phase library methods, synthetic library methods requiring deconvolution, the "one-bead one-compound" library method, and synthetic library methods using affinity chromatography selection (Lam, Anti-Cancer Drug Design, 1997, 12:145). Alternatively, libraries of natural compounds in the form of bacterial, fungal, plant and animal extracts are available or readily produced. Additionally, natural and synthetically produced libraries and compounds can be readily modified through conventional chemical, physical and biochemical means.

Further, known pharmacological agents can be subjected to directed or random chemical modifications, such as acylation, alkylation, esterification, amidation, etc. to produce structural analogs of the agents. Candidate compounds can be selected randomly or can be based on existing compounds that bind to and/or modulate the function of TRPV2 activity. Therefore, a source of candidate agents is one or more than one library of molecules based on one or more than one known compound that increases or decreases TRPV2 protein expression and/or G-protein coupled receptor activity in which the structure of the compound is changed at one or more than one position of the molecule to contain more or fewer chemical moieties or different chemical moieties. The structural changes made to the molecules in creating the libraries of analog activators/inhibitors can be directed, random, or a combination of both directed and random substitutions and/or additions. One of ordinary skill in the art in the preparation of combinatorial libraries can readily prepare such libraries based on the existing compounds.

Assays for the identification of TRPV2 modulators, such as antagonists and agonists, can be carried out manually or using an automated system. Automated systems are preferred if high throughput screenings are performed. For example, one type of automated system utilizes multi-well culture plates, for example, 96-well, 384-well or 1536-well culture plates, wherein each well can contain cells that express TRPV2 endogenously, recombinant cells having a nucleic acid encoding the TRPV2 protein or the purified TRPV2 protein.

The purified TRPV2 protein, antibodies against TRPV2 polypeptides disclosed herein and the various constructs used to express TRPV2 can be used in studies for understanding the mechanism of action of an identified TRPV2 modulator such as an agonist or antagonist as well as understanding the function of the protein.

After a compound has been identified that meets the desired criteria for modulating TRPV2 expression or activity, the compound can then be administered to a live subject, such as a living cell or other organism, or to cultured cells or tissues expressing TRPV2 to assess the efficacy. This can be useful to establish toxicity and other pharmacological parameters of the compound important for determining dosing regimens. For example, after a compound is identified using an ex vivo system containing a TRPV2 polypeptide, the compound can be administered to a culture of cells or an organism to examine various pharmacological aspects of the compound. Additionally, animal models can be used in conjunction with the nucleotides, antibodies and kits described herein to assess the toxicity of a compound. The TRPV2 systems as described herein are particularly advantageous for identifying and establishing dosing regimens in humans, because animals, particularly large specie, such as canines and primates, can be used, which are closer in weight to humans, compared with rats or mice, and therefore provide a more suitable animal model for estimating human dosing.

In another embodiment, the invention provides a method of identifying a compound useful for treating certain types of pain or painful conditions, including but not limited to neuropathic pain and inflammatory pain, comprising the steps of: (a) contacting a sample expressing TRPV2 with a test compound; and (b) determining whether the test compound increases or decreases the expression or activity of TRPV2. In some embodiments, the method further comprises the steps of: (a) administering the test compound to an animal; and (b) determining the extent to which the test compound affects the nociceptive status of the animal.

Various animal models of pain exist, for example, the spinal nerve ligation (SNL) model of nerve injury, which is a neuropathic pain model in rats developed by Kim and Chung (Pain, 50:355-363, 1992). Other suitable animal models of pain can be utilized in connection with the teachings herein. Commonly studied rodent models of neuropathic pain include the chronic constriction injury (CCI) or Bennett model; neuroma or axotomy model; and the partial sciatic transection or Seltzer model (Shir et al., *Neurosci. Lett.*, 115: 62-67, 1990). Exemplary neuropathic pain models include several traumatic nerve injury preparations (Bennett et al., Pain 33: 87-107, 1988; Decosterd et al., Pain 87: 149-58, 2000; Kim et al., Pain 50: 355-363, 1992; Shir et al., Neurosci Lett 115: 62-7, 1990), neuroinflammation models (Chacur et al., Pain 94: 231-44, 2001; Milligan et al., Brain Res 861: 105-16, 2000) diabetic neuropathy (Calcutt et al., Br J Pharmacol 122: 1478-82, 1997), virus-induced neuropathy (Fleetwood-Walker et al., J Gen Virol 80: 2433-6, 1999), vincristine neuropathy (Aley et al., Neuroscience 73: 259-65, 1996; Nozaki-Taguchi et al., Pain 93: 69-76, 2001), and paclitaxel neuropathy (Cavaletti et al., Exp Neurol 133: 64-72, 1995), as well as acute nociceptive tests models and inflammatory models, such as those in which inflammation is produced by an injection of carrageenan, complete Freund's adjuvant (CFA), zymosan or capsaicin (Brennan, T. J. et al. *Pain* 64:493, 1996; D'Amour, F. E. and Smith, D. L. *J Pharmacol* 72: 74-79, 1941; Eddy, N. B. et al. *J Pharmacol Exp Ther* 98:121, 1950; Haffner, F. *Dtsch Med Wochenschr* 55:731, 1929; Hargreaves, K. et al. *Pain* 32: 77-88, 1988; Hunskaar, S. et al. *J Neurosci Meth* 14:69, 1985; Randall, L. O. and Selitto, J. J. *Arch. Int. Pharmacodyn* 111: 409-419, 1957; Siegmund, E. et al. *Proc Soc Exp Bio Med* 95:729, 1957). In another aspect, the animal model involves a dog, or a primate, for example, a canine or a human.

Therapeutic efficacy and toxicity can be determined by standard pharmaceutical procedures in cell cultures or experimental animals by calculating, for example, the $ED_{50}$ (the dose therapeutically effective in 50% of the population or the dose that produces 50% of the maximal desired effect) and the $LD_{50}$ (the dose lethal to 50% of the population). The dose ratio between toxic and therapeutic effects is the therapeutic index, and can be expressed as the ratio, $LD_{50}/ED_{50}$. The data obtained from cell culture assays using TRPV2 polypeptide, cells expressing TRPV2 and/or animal studies, such as canine or primate studies, are used in formulating a range of dosage for human use. The dosage contained in such compositions preferably gives rise to a range of circulating concentrations that include and/or exceed the $ED_{50}$ with little or no toxicity. The dosage varies within this range depending upon the dosage form employed, sensitivity of the patient and the route of administration.

The exact dosage will be determined by the one administering the dose, in light of factors related to the subject requiring treatment. Dosage and administration are adjusted to provide sufficient levels of the active agent or to maintain the desired effect, for example, control of pain levels. Factors that can be taken into account include the general health, age, weight and gender of the subject, diet, time and frequency of administration, drug combination(s), reaction sensitivities and tolerance/response to therapy.

The pharmaceutical compositions containing a compound that has been identified as modulating TRPV2 expression or activity can be administered by any number of routes, including, but not limited to, oral, intravenous, intramuscular, intraarticular, intraarterial, intramedullary, intrathecal, epidural, intraventricular, transdermal, subcutaneous, intraperitoneal, intranasal, enteral, topical, sublingual, inhalational, intraocular, intra-aural or rectal means.

In addition to the active ingredients, these pharmaceutical compositions can contain suitable, pharmaceutically acceptable carriers comprising excipients and auxiliaries that facilitate processing of the active compounds into preparations that can be used pharmaceutically or that facilitate absorption or distribution of the active compounds. Further details on techniques for formulation and administration can be found in Remington's Pharmaceutical Sciences, $20^{th}$ edition, Maack Publishing Co., Easton, Pa. (2000). Pharmaceutical compositions for oral administration can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for ingestion by the patient.

EXAMPLE 1

The present invention is directed to an isolation of a cDNA from canine dorsal root ganglion (DRG) tissue (SEQ ID NO: 1) encoding a full length TRPV2 (SEQ ID NO: 2), its preparation, characterization and functional expression, the establishment of a high throughput assay for testing the ability of compounds to alter the function of TRPV2 and the evaluation for the potential to decrease pain in animals and humans. In order to clone TRPV2 from canine, messenger RNA was first isolated from canine DRG, a reverse transcriptional PCR (RT-PCR) and a Rapid Amplification of cDNA End (RACE-PCR) technique were used. The cloning result revealed that the open reading frame cTRPV2 contains 2298 bp encoding a polypeptide of 765 amino acids and having a calculated molecular mass of 85.4 kDa. A Kyte-Doolitle hydrophilicity analysis of primary sequence predicts the presence of six putative hydrophobic domains clustered near the carboxyl terminus, which may form a pore of the ion channel. The nucleotide sequence of canine TRPV2 is 83%, 82% and 86% identical to the mouse, rat and human TRPV2, respectively. (See FIG. 5).

A. Isolation of Poly(A+) RNA

As a first step in the cloning of cTRPV2, poly(A+) RNA was isolated from 100 µg of total RNA from canine DRG (Custom made by *Analytical Biological Service* Inc. DE) using an Oligotex spin column (Qiagen Inc., CA). Briefly, 150 µl of RNase-free water, 250 µl of buffer OBB, containing 20 mM Tris (pH=7.5), 1M NaCl, 2 mM EDTA and 0.2% SDS, and 15 µl of a suspension of Oligotex beads were added to 100 µl of total RNA solution (1 µg/µl). The RNA/Oligotex bead mixture was then heated at 70° C. for 3 min, to disrupt any secondary structure of the RNA, followed by incubation at room temperature for 10 min. The poly (A+) RNA/Oligotex particle complex was centrifuged and washed twice with 400 µl of buffer OW2, containing 10 mM Tris (pH=7.5), 150 mM NaCl and 1 mM EDTA, and then transferred to a spin column for the elution step. The poly(A+) RNA was eluted from Oligotex bead using 200 µl of prewarmed (70° C.) buffer OEB, containing 5 mM Tris (pH=7.5). Finally, canine DRG poly(A+) RNA was precipitated by ethanol in the presence of 20 µg of glycogen and 150 mM sodium acetate and resuspended in 10 µl of RNase-free water.

B. Synthesis of Double-Stranded cDNA

4 µl (1 µg) of canine DRG poly(A+) RNA and 1µl of cDNA synthesis primer, a 52-mer oligo with sequence of 5'-TTCTAGAATTCAGCGGCCGC(T)$_{30}$N$_{-1}$N-3' (SEQ ID NO: 12), N$_{-1}$=G, A or C; and N=G, A, C or T (Clontech, CA SEQ ID NO: 12), were mixed, incubated at 70° C. for 2 min and then cooled on ice for 2 min. The first strand cDNA synthesis (reverse transcription) was performed at 42° C. for 1 hour using 20 units of AMV reverse transcriptase in the presence of 1 mM dNTP mixture and first strand synthesis buffer, containing 50 mM Tris (pH =8.5), 8 mM MgCl$_2$, 30 mM KCl and 1 mM DTT, in 10 µl. The second strand cDNA synthesis was performed by adding an enzyme cocktail, consisting of 24 units of E. coli DNA polymerase I, 5 units of *E. coli* DNA ligase I unit of *E. coli* RNase H, 0.25 mM of dNTP mixture (0.25 mM of each dATP, dCTP, dGTP, and dTTP) and second strand buffer, containing 100 mM KCl, 10 mM ammonium sulfate, 5 mM MgCl$_2$, 0.15 mM β-NAD, 20 mM Tris (pH =7.5) and 50 pM bovine serum albumin, in 80 µl. The reaction was first carried out at 16° C. for 90 min followed by addition of 20 units of T4 DNA polymerase, with continued incubation at the same temperature for 45 min. The reaction was terminated by adding 10 mM EDTA and 8 µg of glycogen. Phenol and chloroform extractions were performed, followed by ethanol precipitation. Double-stranded cDNA was then suspended in 200µl of TE buffer and stored at −20° C.

C. PCR Amplification of Near Carboxyl Terminus of cTRPV2

A TRPV2 cDNA fragment was successfully amplified by PCR using two primers designated as forward primer dv2-6 (5'-TGATGATCGCAGACAACT CAGCCGAGAACA-3') (SEQ ID NO: 5), corresponding to nucleotides 761-790 of SEQ ID NO 1, and reverse primer dv2-8 (5'-GGACAGCTGGGCCTGATGGC TCTTCA-3') (SEQ ID NO: 6), corresponding to nucleotides 2175-2200 of SEQ ID NO 1. The PCR reaction was performed in a final volume of 50 µl, containing 5 µl of canine DRG double-stranded cDNA, 5 µl of 10× reaction buffer (provided with Advantage2 DNA polymerase), 200 µM dNTPs, 200 nM forward primer dv2-6, 200 nM reverse primer dv2-8 and 1 µl of 50× Advantage™2 DNA polymerase mixture (Clontech, Calif.). PCR was performed by an initial denaturing step at 94° C. for 1 min, followed by 30 cycles of: (a) denaturing at 94° C. for 30 sec, (b) annealing at 55° C. for 30 sec and (c) extension at 72° C. for 60 sec. Agarose gel electrophoresis was performed, which revealed that the PCR product was approximately 1.44 kb. After PCR, the 1.44 kb PCR fragment was purified and subcloned into pCRII TA cloning vector (Invitrogen, CA) following the vendor's protocol. Six independent clones were picked and subjected to DNA sequencing analysis. The sequence results revealed that the PCR amplified fragment was 82%, 81% and 87% identical to the comparable region, i.e., near carboxyl termini of mouse, rat and human TRPV2, respectively.

D. RACE-PCR of 5' and 3' Ends of cTRPV2 Sequence

To obtain the complete 5' and 3' cDNA sequences of the cTRPV2 gene, RACE-PCR technology was performed. First, both 5'- and 3'-RACE-Ready cDNAs were synthesized separately with SMART™ RACE DNA Amplification Kit (BD Clontech, Calif.), according to the manufacturer's instructions. To prepare cDNA for 5' RACE, in one 0.5 ml tube, 3 µl of dog DRG poly(A+) RNA obtained in step A above was mixed with 1 µl of 5'-CDS primer and 1 µl of SMART II A oligo. To prepare cDNA for 3' RACE, 3 µl of canine DRG poly(A+) RNA was mixed with 1 µl 3'-CDS primer and 1 µl RNase free water in another 0.5 ml tube and then incubated at 70° C. for 2 min, followed by cooling on ice for 2 min. Next, 2 µl of 5× First Strand buffer, 1 µl 20 mM DTT, 1 µl of 10 mM dNTP mix and 1 µl PowerScript Reverse Transcriptase were added to each tube, and synthesis was performed at 42° C. for 90 min. The reactions were stopped by adding 200 µl of TE buffer and heating the sample to 72° C. for 7 min. The reaction products were stored at −20° C. All of the oligos, 5'-CDS, 3'-CDS and SMARTII were provided by Clontech.

For RACE-PCR, two primers were synthesized based on the above 1.44 kb cDNA sequence the cTRPV2 cDNA. The forward primer for 3' RACE-PCR was dv2-6; the reverse primer for 5'-RACE-PCR was named dv2-2 (5'-GATTTTGCCCTCCTTGGCAGCCAG-3') (SEQ ID NO: 7), which corresponds to nucleotides 901-924 of SEQ ID NO: 1. Both 5' and 3'-RACE PCRs were performed in a final volume of 50 µl, containing 2.5 µl of cDNA template (either 5'- or 3'-RACE-Ready cDNA, as described above), 5 µl of 10× reaction buffer, 200 µM dNTPs, 200 nM Universal Primer Mix (UPM) (Clontech), 200 nM cTRPV2 specific primer (dv2-2 for 5'-RACE PCR or dv2-2 for 3'-RACE PCR) and 1 µl of 50× Advantage™-HF2 DNA polymerase mixture (Clontech). The thermal cycler parameter for the RACE-PCR was 25 cycles of 94° C. for 30 sec and 68° C. for 3 min. After the RACE-PCR reaction, the products were diluted 50-fold and used for the next round nested PCR. For nested PCR, two oligos were synthesized. They were reverse primer dv2-9 (5'-TTGCCAGAGTTCCGGTCGATCTGAAGCA-3') (SEQ ID NO: 8), used for the 5'-nested-PCR and forward primer dv2-10 (5'-TCCAAGACCAGCTGCGCTTCCGC GGCGT-3') (SEQ ID NO: 9) used for the 3' nested-PCR. Both 5' and 3'-nested-PCRs were performed in a final volume of 50 µl, containing 5 µl of a 1:50 dilution of the previous RACE-PCR product, 5 µl of 10× reaction buffer, 200 µM dNTPs, 200 nM Universal Primer Mix (UPM) (Clontech), 200 nM cTRPV2 specific primer (dv2-9 for 5' nested-PCR or dv2-10 for 3' nested-PCR) and 1 µl of 50× Advantage2™ DNA polymerase mixture (Clontech). The thermal cycler parameters for the RACE-PCR were 20 cycles of 94° C. for 30 sec and 68° C. for 3 min. The nested-PCR products were purified and directly subcloned into pCRII TA cloning vector (Invitrogen). Eight to eighteen independent clones from either 5'-RACE/nested or 3'-RACE/nested PCR were picked and subjected to DNA sequencing analysis.

E. Sequence of Full-Length cTRPV2 cDNA:

The sequence of the full-length canine TRPV2 cDNA was confirmed by synthesizing PCR primers based on the sequence of the 5' and 3' ends obtained by RACE-PCR. Full length cTRPV2 cDNA was amplified from canine DRG double-stranded cDNAs prepared in step B above by high-fidelity DNA polymerase using two sets of primers. The first primer set was forward primer dv2-1 (5'-ATGGCCTCGC CCTCCAGCTC TCCCA-3') (SEQ ID NO: 10) and reverse primer dv2-2 for amplification of a 924 bp cDNA fragment encoding cTRPV2 amino terminal 308 residues; the second primer set was forward primer dv2-6 and reverse primer dv2-11 (5'-TTAGTGGGACTTCA GGAGCTGGAGG GGC-3') (SEQ ID NO: 11) for amplification of a 1.54 kb cDNA fragment encoding cTRPV2 carboxyl terminal 512 residues. The PCR was performed in a final volume of 50 µl, containing 5 µl of above canine DRG double-stranded cDNAs (prepared as above), 5 µl of 10× reaction buffer, 200 µM dNTP, 200 nM forward primer (either dv2-1 or dv2-6) and reverse primer (either dv2-2 or d2-11), and 1 µl of 50× Advantage™-HF2 DNA polymerase mixture (Clontech, Calif.). The PCR was performed by an initial denaturing step at 94° C. for 2 min, followed by 35 cycles of denaturing at 94° C. for 30 sec and annealing and extension at 70° C. for 5 min. After PCR, the 2.3 kb PCR fragment was purified and subcloned into pCRII TA cloning vector, following the same cloning protocol as in step C above. Several independent clones were picked and subjected to DNA sequencing analysis. The clones NQC881 and NQC918 were used for further subcloning and studying. The sequence results revealed that the open reading frame nucleic acid sequence of cTRPV2 cDNA SEQ ID NO 1 was 83%, 82% and 86% identical to the cDNA sequences of mouse (Accession number: BC005415), rat (Accession number: AF129113) and human (Accession number: AF129112; SEQ ID NO: 3) TRPV2, respectively. (See FIG. 5).

F. Sequence Analysis

5'- and 3'-RACE-PCR facilitated the determination of the 68 bp sequence of the 5' untranslated region; 3'-RACE-PCR allowed for the determination of the 431 bp sequence of the 3' untranslated region, including the 37-mer poly(A+) tail. No in-frame stop codon was identified in either 5' or 3' untranslated region.

The predicted cTRPV2 open reading frame consists of a 2298 bp sequence that is predicted to encode a polypeptide of 765 amino acids (SEQ ID NO: 2), having a calculated molecular mass of 85.4 kDa. A Kyte-Doolitle hydrophilicity analysis (not shown) of primary sequence predicts the presence of six putative hydrophobic (or transmembrane) domains clustered at the carboxyl half of the molecule and believed to form the pore of the ion channel.

The cTRPV2 amino acid sequence was aligned with the human (GenBank Acc. No.: AF129112; SEQ ID NO: 4), rat (GenBank Acc. No.: AF129113), and mouse (GenBank Acc. No.: BC005415) sequences, which revealed 84%, 81% and 83% sequence identity, respectively (FIG. 5), using the Gap program from Seqweb version 2 of Accelrys. The Gap program uses the algorithm of Needleman and Wunsch (J Mol. Biol., 48:443 (1970)) to find the alignment of two complete sequences, by maximizing the number matches and minimizing the number of gaps. A search of canine genomic sequence with TRPV2 cDNA revealed that cTRPV2 is located at chromosome 5, spanning 17435 bp with a total of 14 exons.

EXAMPLE 2

Recombinant Expression of cTRPV2

A. Cloning of Canine TRPV2 into a Mammalian Expression Vector

For expression of cTRPV2 in mammalian cell lines, the full-length cDNA of cTRPV2 was subcloned into pcDNA3.1 (neo) by performing a three-way ligation. First, the clone NQC881 was digested with NotI and XhoI to yield a 0.9 kb 5' fragment, and the clone NQC918 was digested with XhoI and EcoRI to yield a 1.45 kb 3' fragment. The 0.9 kb 5' and 1.45 kb 3' cTRPV2 fragments were purified and ligated with pcDNA3.1 that was predigested with NotI and EocRI, creating the expression construct cTRPV2/pcDNA3.1.

B. Transient Transfection of Expression Construct into Mammalian Cells

The expression construct, cTRPV2/pcDNA3.1 was then transfected into human embryonic kidney cells (HEK293, ATCC CRL-1573) with FuGene6 transfection reagent (Roche, Indianapolis, Ind.), according to the vendor's protocol. TRPV2-expressing HEK293 cells were cultured in DMEM supplemented with 10% fetal bovine serum, 100 units/ml penicillin and 100 µg/ml streptomycin at 37° C. with 5% $CO_2$, and were analyzed using a calcium influx assay 48-72 hr. post-transfection.

EXAMPLE 3

Calcium Influx Functional Assay of cTRPV2

To demonstrate the functionality of the cTRPV2 gene, HEK293 cells were transiently transfected with plasmids encoding either cTRPV2 or vector control and then evaluated in a FLIPR assay to measure changes in intracellular calcium levels of the cells in each well upon addition of agonist. Transiently transfected cells were seeded in 384-well plates at a density of 1×10$^4$ cells/well and incubated overnight at 37° C. The following day, the cells were loaded with buffer and calcium dye, as recommended by the vendor (Molecular Devices, Sunnyvale, Calif.), in a final volume of 40 µl and incubated for 30 minutes at room temperature. The fluorescence intensity was measured by FLIPR before, during and after the addition of $\Delta^9$-THC, which was added to the cells at a final concentration of 100 µM. The results are shown in FIG. 6.

EXAMPLE 4

A Screening Assay for a Desensitizer or Inactivator of a TRPV2 Channel

Generally, upon prolonged exposure of an ion channel to an activating stimulus (e.g., an agonist) or in response to a direct desensitizing or inactivating stimulus, the channel may assume alternate conformations that are variably less activatable in response to an activating stimulus. These less activatable or inactivatable conformations may be referred to functionally as being desensitized or inactivated, and compounds that produce these states as being desensitizers or inactivators, respectively. Such conformations may be induced or stabilized by or in the presence of these so-called desensitizers or inactivators, and may arise by the preferential action of the desensitizer or inactivator upon an open or upon a closed channel. In addition, such conformations may be reversible, across variable time courses and conditions, or may be irreversible, pending de novo synthesis of nascent channels. Compounds that are identified as desensitizers or inactivators, either being reversible or irreversible, may be useful in the treatment of certain conditions, including pain conditions, in which decreased TRPV2 activity would be therapeutic.

Therefore, in another embodiment, the invention provides a method of identifying reversible and irreversible desensitizers or inactivators of cTRPV2 activity. The first method is designed to identify compounds that induce and/or stabilize the channel in a desensitized or inactivated state from a closed state and comprises the steps of: (a) providing a recombinant cell comprising a nucleic acid encoding a cTRPV2 protein, (b) contacting the recombinant cell at a temperature above the threshold for activation (typically above about 52° C.) with a test compound for varying lengths of time, (c) contacting the recombinant cell with agonist for activation in the presence of a test compound for varying lengths of time, (d) extensively washing out the test compound and (e) at varying time points, determining the extent to which the test compound diminishes TRPV2 activity in response to a subsequent exposure to a TRPV2-activating stimulus. The second method is designed to identify compounds that induce and/or stabilize the channel in a desensitized or inactivated state from an open state and comprises EITHER the steps of: (a) providing a recombinant cell comprising a nucleic acid encoding a cTRPV2 protein, (b) contacting the recombinant cell at a temperature above the threshold for activation (typically above about 52° C.) or with a TRPV2 agonist, (c) contacting the recombinant cell with a test compound for varying lengths of time, (d) extensively washing out the test compound and agonist and (e) at varying time points, determining the extent to which the test compound diminishes TRPV2 activity in response to a subsequent exposure to a TRPV2-activating stimulus OR the steps of: (a) providing a recombinant cell comprising a nucleic acid encoding a cTRPV2 protein, (b) incubating the recombinant cell at a temperature below the threshold for activation, (c) contacting the recombinant cell with a test compound for varying lengths of time, (d) extensively washing out the test compound and (e) at varying time points, determining the extent to which the test compound diminishes TRPV2 activity in response to a subsequent exposure to a TRPV2-activating stimulus.

What is claimed is:

1. A substantially purified nucleic acid molecule comprising a nucleotide sequence selected from the group consisting of:
   (a) a nucleotide sequence having at least 90% sequence identity to SEQ ID NO: 1 and encoding SEQ ID NO: 2; and
   (b) a nucleotide sequence encoding a polypeptide having at least 90% sequence identity to SEQ ID NO: 2;
   wherein said nucleotide sequence encodes a polypeptide with TRPV2 activity.

2. The nucleic acid molecule of claim 1, comprising a nucleotide sequence having at least 90% sequence identity to SEQ ID NO: 1 and encoding SEQ ID NO: 2.

3. The nucleic acid molecule of claim 2, comprising SEQ ID NO: 1.

4. The nucleic acid molecule of claim 1, comprising a nucleotide sequence encoding a polypeptide having at least 90% sequence identity to SEQ ID NO: 2.

5. The nucleic acid molecule of claim 4, comprising a nucleotide sequence encoding SEQ ID NO: 2.

6. An expression vector comprising the nucleic acid molecule of claim 1.

7. The expression vector of claim 6, comprising a nucleotide sequence having at least 90% sequence identity to SEQ ID NO: 1 and encoding SEQ ID NO: 2.

8. The expression vector of claim 7, comprising SEQ ID NO: 1.

9. The expression vector of claim 6, comprising a nucleotide sequence encoding a polypeptide having at least 90% sequence identity to SEQ ID NO: 2.

10. The expression vector of claim 9, comprising a nucleotide sequence encoding SEQ ID NO: 2.

11. A recombinant host cell comprising the nucleic acid molecule of claim 1.

12. The recombinant host cell of claim 11, comprising a nucleotide sequence having at least 90% sequence identity to SEQ ID NO: 1 and encoding SEQ ID NO: 2.

13. The recombinant host cell of claim 12, comprising SEQ ID NO: 1.

14. The recombinant host cell of claim 11, comprising a nucleotide sequence encoding a polypeptide having at least 90% sequence identity to SEQ ID NO: 2.

15. The recombinant host cell of claim 14, comprising a nucleotide sequence encoding SEQ ID NO: 2.

16. A method of identifying a compound that increases or decreases the conductivity of a cTRPV2 channel, comprising the steps of:
   (a) contacting a test compound with the recombinant host cell of claim 11; and
   (b) determining whether the test compound increases or decreases the conductivity of the cTRPV2 channel.

17. The method of claim 16 wherein the recombinant host cell comprises a nucleotide sequence having at least 90% sequence identity to SEQ ID NO: 1 and encoding SEQ ID NO: 2.

18. The method of claim 16 wherein the recombinant host cell comprises SEQ ID NO: 1.

19. The method of claim 16 wherein the recombinant host cell comprises a nucleotide sequence encoding a polypeptide having at least 90% sequence identity to SEQ ID NO: 2.

20. The method of claim 16 wherein the recombinant host cell comprises a nucleotide sequence encoding SEQ ID NO: 2.

21. The method of claim 16 wherein step (b) comprises determining intracellular calcium levels.

22. The method of claim 21 wherein the intracellular amount of calcium is determined using a calcium fluorescence assay.

23. The method of claim 21 wherein the intracellular amount of calcium is determined using a radioactive $Ca^{2+}$-45 influx assay.

24. The method of claim 16 wherein the step of determining whether the test compound increases of decreases the conductivity of the channel comprises measuring the current conducted by the channel.

25. The method of claim 16 further comprising the step of increasing the conductivity of the channel prior to the step of contacting the test compound with the channel.

26. The method of claim 25 wherein the step of increasing the conductivity of the channel comprises depolarizing the channel.

27. The method of claim 25 wherein the compound capable of increasing the conductivity of the channel is selected from the group consisting of cannabinol, cannabidiol, $\Delta^9$-THC, O-1821 and 2-APB.

28. The method of claim 25 wherein the step of increasing the conductivity of the channel comprises incubating the channel at a cTRPV2 channel activating temperature.

29. The method of claim 28 wherein the cTRPV2 activating temperature is 52-55° C.

* * * * *

SEQUENCE LISTING

```
<160> NUMBER OF SEQ ID NOS: 12

<210> SEQ ID NO 1
<211> LENGTH: 2443
<212> TYPE: DNA
<213> ORGANISM: Canis familiaris
<220> FEATURE:
<221> NAME/KEY: CDS
<222> LOCATION: (14)..(2308)

<400> SEQUENCE: 1
acgcgggggt agg atg gcc tcg ccc tcc agc tct ccc act ttc agg ctt          49
            Met Ala Ser Pro Ser Ser Ser Pro Thr Phe Arg Leu
              1               5                  10 gag aca tca gat gga ggc cag gaa gat ggc agt gag gtg gac aaa aga        97
Glu Thr Ser Asp Gly Gly Gln Glu Asp Gly Ser Glu Val Asp Lys Arg
        15                  20                  25 aag gct ggc ccg ggg gct ggg cca ccc ccc atg gag tca cca ttc caa       145
Lys Ala Gly Pro Gly Ala Gly Pro Pro Pro Met Glu Ser Pro Phe Gln
 30                  35                  40 ggg gag gat cgc aaa tgc tct cct cag atc aaa gta aac ctc aac ttc       193
Gly Glu Asp Arg Lys Cys Ser Pro Gln Ile Lys Val Asn Leu Asn Phe
 45                  50                  55                  60 cgc aaa gga gca ggt gtc agc cag ccg gac cca aac cgc ttt gac cgt       241
Arg Lys Gly Ala Gly Val Ser Gln Pro Asp Pro Asn Arg Phe Asp Arg
                 65                  70                  75 gat cgg ctc ttc agc gtg gtt gcc cgg ggt gtc ccc gag gat ctg gct       289
Asp Arg Leu Phe Ser Val Val Ala Arg Gly Val Pro Glu Asp Leu Ala
             80                  85                  90 ggg tta cca gag tac ctg tcc cgg acc agc aag tac ctc acc gac tca       337
Gly Leu Pro Glu Tyr Leu Ser Arg Thr Ser Lys Tyr Leu Thr Asp Ser
         95                  100                 105 gag tac aca gag ggc tcc aca ggc aag acg tgc ctg atg aag gct gtg       385
Glu Tyr Thr Glu Gly Ser Thr Gly Lys Thr Cys Leu Met Lys Ala Val
    110                 115                 120 tta aac ctt cgg gat ggt gcc aac gcc tgc atc ctg cca ttg ctt cag       433
Leu Asn Leu Arg Asp Gly Ala Asn Ala Cys Ile Leu Pro Leu Leu Gln
125                 130                 135                 140 atc gac cgg aac tct ggc aat ccc cag ccc ctg gtc aat gcc caa tgc       481
Ile Asp Arg Asn Ser Gly Asn Pro Gln Pro Leu Val Asn Ala Gln Cys
                145                 150                 155 acg gat gag tac tac cga ggc cac agt gcc ctg cat att gcc atc gag       529
Thr Asp Glu Tyr Tyr Arg Gly His Ser Ala Leu His Ile Ala Ile Glu
            160                 165                 170
```

-continued

```
aag agg agc ctg cag tgt gtg aag ctc ttg gtg gag aac ggg gcc aat      577
Lys Arg Ser Leu Gln Cys Val Lys Leu Leu Val Glu Asn Gly Ala Asn
        175                 180                 185 gtg cat gcc cag gcc tgt ggc caa ttc ttc cag aaa aag agc caa ggg      625
Val His Ala Gln Ala Cys Gly Gln Phe Phe Gln Lys Lys Ser Gln Gly
    190                 195                 200 act tgc ttc tac ttt ggt gag ctg ccc ctc tct ctg gct gcg tgc acc      673
Thr Cys Phe Tyr Phe Gly Glu Leu Pro Leu Ser Leu Ala Ala Cys Thr
205                 210                 215                 220 aag cag tgg gat gtg gtg acc tac ctc ctg gag aac ccg cat cag cct      721
Lys Gln Trp Asp Val Val Thr Tyr Leu Leu Glu Asn Pro His Gln Pro
                225                 230                 235 gcc agc ctg cag gca gcc gac tcg ctg ggc aac acg gcc ctg cat gcc      769
Ala Ser Leu Gln Ala Ala Asp Ser Leu Gly Asn Thr Ala Leu His Ala
            240                 245                 250 ttg gtg atg atc gca gac aac tca gcc gag aac agt gcc ctg gtg atc      817
Leu Val Met Ile Ala Asp Asn Ser Ala Glu Asn Ser Ala Leu Val Ile
        255                 260                 265 cgc atg tat gat gcg ctc ctc cgt gct ggg gcc cgc ctc tgc ccc aaa      865
Arg Met Tyr Asp Ala Leu Leu Arg Ala Gly Ala Arg Leu Cys Pro Lys
270                 275                 280 gtg cag ctc gag gac atc ccc aac ctg cag ggc ctc acg ccc ctg aag      913
Val Gln Leu Glu Asp Ile Pro Asn Leu Gln Gly Leu Thr Pro Leu Lys
285                 290                 295                 300 ctg gct gcc aag gag ggc aaa atc gag att ttc agg cac atc ctg cag      961
Leu Ala Ala Lys Glu Gly Lys Ile Glu Ile Phe Arg His Ile Leu Gln
                305                 310                 315 cgg gag ttc tcg ggg ccg tgc cag tca ctt tcc cga aag ttt act gag     1009
Arg Glu Phe Ser Gly Pro Cys Gln Ser Leu Ser Arg Lys Phe Thr Glu
            320                 325                 330 tgg tgc tac ggg cct gtc cgg gtg tcg ctg tat gac ctg gcc tct gtg     1057
Trp Cys Tyr Gly Pro Val Arg Val Ser Leu Tyr Asp Leu Ala Ser Val
        335                 340                 345 gac agc tgg gag gag aac tcc gtg ctg gag atc atc gcc ttt cat tgc     1105
Asp Ser Trp Glu Glu Asn Ser Val Leu Glu Ile Ile Ala Phe His Cys
350                 355                 360 aga agc ccg cac cga cac cga atg gtg gtt ttg gaa cca ctg aac aaa     1153
Arg Ser Pro His Arg His Arg Met Val Val Leu Glu Pro Leu Asn Lys
365                 370                 375                 380 ctg cta cag gcg aaa tgg gat ctg cta atc ccc aga ttc ttc ttc aac     1201
Leu Leu Gln Ala Lys Trp Asp Leu Leu Ile Pro Arg Phe Phe Phe Asn
                385                 390                 395 ttc ctg tgt tac ctg acc tac atg ttc atc ttt acc gct gtt gct tac     1249
Phe Leu Cys Tyr Leu Thr Tyr Met Phe Ile Phe Thr Ala Val Ala Tyr
            400                 405                 410 cac cag cca gcc ctg ggg aag gcc ttc ctc ccc ccg act gtg act act     1297
His Gln Pro Ala Leu Gly Lys Ala Phe Leu Pro Pro Thr Val Thr Thr
        415                 420                 425 ggg gac tcc atg ctg ctg ctg ggc cac atc ctg atc ctc ctt ggg ggg     1345
Gly Asp Ser Met Leu Leu Leu Gly His Ile Leu Ile Leu Leu Gly Gly
430                 435                 440 gtc tac ctc ttg gtg ggc cag cta tgg tac ttc tgg agg cgt cgt ctg     1393
Val Tyr Leu Leu Val Gly Gln Leu Trp Tyr Phe Trp Arg Arg Arg Leu
445                 450                 455                 460 ttc atc tgg atc tcc ttc gtg gac agc tac ttt gaa ctg ctc ttc ctg     1441
Phe Ile Trp Ile Ser Phe Val Asp Ser Tyr Phe Glu Leu Leu Phe Leu
                465                 470                 475 gtc cag gcc ctg ctc aca gtg ctg tcc cag gga ctg tgt ttc ctg gcc     1489
Val Gln Ala Leu Leu Thr Val Leu Ser Gln Gly Leu Cys Phe Leu Ala
            480                 485                 490
```

```
gtg gag tgg tac ctg cct ctg ctt gtg tct tcc ctg gtg ctg ggc tgg    1537
Val Glu Trp Tyr Leu Pro Leu Leu Val Ser Ser Leu Val Leu Gly Trp
        495                 500                 505 ctg aac ctg ctc tat tac aca cgc ggc ttg cag cac aca ggc atc tac    1585
Leu Asn Leu Leu Tyr Tyr Thr Arg Gly Leu Gln His Thr Gly Ile Tyr
    510                 515                 520 agt gtc atg atc cag aag gtc atc ctg cgg gac ctg ctc cgc ttc ctg    1633
Ser Val Met Ile Gln Lys Val Ile Leu Arg Asp Leu Leu Arg Phe Leu
525                 530                 535                 540 ctg gtc tac tta gtc ttc ctg ttt ggc ttc gct gta gcc ctg gtg agc    1681
Leu Val Tyr Leu Val Phe Leu Phe Gly Phe Ala Val Ala Leu Val Ser
                545                 550                 555 ctg agc cgg gaa gcc cga gac tct ggg gtc ccc aca ggc ccc aat gtc    1729
Leu Ser Arg Glu Ala Arg Asp Ser Gly Val Pro Thr Gly Pro Asn Val
            560                 565                 570 acg gag gca gcg cag tct ggg gca gga cag ggg gac gag gag ggc agc    1777
Thr Glu Ala Ala Gln Ser Gly Ala Gly Gln Gly Asp Glu Glu Gly Ser
        575                 580                 585 tcc tcc cca tac ggt ggc ata ctg gac gct tcc ttg gag ctc ttc aag    1825
Ser Ser Pro Tyr Gly Gly Ile Leu Asp Ala Ser Leu Glu Leu Phe Lys
    590                 595                 600 ttc acc atc ggc atg ggg gag ctg gca ttc caa gac cag ctg cgc ttc    1873
Phe Thr Ile Gly Met Gly Glu Leu Ala Phe Gln Asp Gln Leu Arg Phe
605                 610                 615                 620 cgc ggc gtg gtg cta ctg ctc ctg gcc tat gtg ctg ctc acc tac        1921
Arg Gly Val Val Leu Leu Leu Leu Ala Tyr Val Leu Leu Thr Tyr
                625                 630                 635 atc ctg ctg ctc aat atg ctc atc gcc ctc atg agc gag acc gtc aac    1969
Ile Leu Leu Leu Asn Met Leu Ile Ala Leu Met Ser Glu Thr Val Asn
                640                 645                 650 agt gtt gcc agt gac agc tgg agc atc tgg aag ctg cag aaa gct atc    2017
Ser Val Ala Ser Asp Ser Trp Ser Ile Trp Lys Leu Gln Lys Ala Ile
        655                 660                 665 tct gtc ctg gag atg gag aat ggc tac tgg tgg tgc agg agg aag aag    2065
Ser Val Leu Glu Met Glu Asn Gly Tyr Trp Trp Cys Arg Arg Lys Lys
    670                 675                 680 cag cgg gcc ggt gtg aag ctg acc gtt ggg acc agg ccg gat ggt agc    2113
Gln Arg Ala Gly Val Lys Leu Thr Val Gly Thr Arg Pro Asp Gly Ser
685                 690                 695                 700 tct gat gag cgc tgg tgc ttc agg gtg gag gaa gtg aac tgg gct gcg    2161
Ser Asp Glu Arg Trp Cys Phe Arg Val Glu Glu Val Asn Trp Ala Ala
                705                 710                 715 tgg gag cag acg ctg cca aca gtg tgt gaa gag cca tca ggc cca gct    2209
Trp Glu Gln Thr Leu Pro Thr Val Cys Glu Glu Pro Ser Gly Pro Ala
            720                 725                 730 gtc cct ggc agc ata agg aac cct gtc ctg gcc tcc caa ccg gag gag    2257
Val Pro Gly Ser Ile Arg Asn Pro Val Leu Ala Ser Gln Pro Glu Glu
        735                 740                 745 gac act gcc tcg gag gaa gac caa ctg ccc ctc cag ctc ctg aag tcc    2305
Asp Thr Ala Ser Glu Glu Asp Gln Leu Pro Leu Gln Leu Leu Lys Ser
    750                 755                 760 cac taatgggcca gttgcacggc agtcaggaaa tcttcccagc cctgcctgct         2358
His
765 ggctctgggg ctccagagaa ctttggtggc aaatgtaaat aaatatcttt tcataaaaaa   2418 aaaaaaaaaa aaaaaaaaaa aaaaa                                        2443

<210> SEQ ID NO 2
<211> LENGTH: 765
```

```
<212> TYPE: PRT
<213> ORGANISM: Canis familiaris

<400> SEQUENCE: 2

Met Ala Ser Pro Ser Ser Ser Pro Thr Phe Arg Leu Glu Thr Ser Asp
  1               5                  10                  15

Gly Gly Gln Glu Asp Gly Ser Glu Val Asp Lys Arg Lys Ala Gly Pro
                 20                  25                  30

Gly Ala Gly Pro Pro Met Glu Ser Pro Phe Gln Gly Glu Asp Arg
             35                  40                  45

Lys Cys Ser Pro Gln Ile Lys Val Asn Leu Asn Phe Arg Lys Gly Ala
         50                  55                  60

Gly Val Ser Gln Pro Asp Pro Asn Arg Phe Asp Arg Asp Arg Leu Phe
 65                  70                  75                  80

Ser Val Val Ala Arg Gly Val Pro Glu Asp Leu Ala Gly Leu Pro Glu
                 85                  90                  95

Tyr Leu Ser Arg Thr Ser Lys Tyr Leu Thr Asp Ser Glu Tyr Thr Glu
                100                 105                 110

Gly Ser Thr Gly Lys Thr Cys Leu Met Lys Ala Val Leu Asn Leu Arg
             115                 120                 125

Asp Gly Ala Asn Ala Cys Ile Leu Pro Leu Leu Gln Ile Asp Arg Asn
         130                 135                 140

Ser Gly Asn Pro Gln Pro Leu Val Asn Ala Gln Cys Thr Asp Glu Tyr
145                 150                 155                 160

Tyr Arg Gly His Ser Ala Leu His Ile Ala Ile Glu Lys Arg Ser Leu
                165                 170                 175

Gln Cys Val Lys Leu Leu Val Glu Asn Gly Ala Asn Val His Ala Gln
             180                 185                 190

Ala Cys Gly Gln Phe Phe Gln Lys Ser Gln Gly Thr Cys Phe Tyr
         195                 200                 205

Phe Gly Glu Leu Pro Leu Ser Leu Ala Ala Cys Thr Lys Gln Trp Asp
    210                 215                 220

Val Val Thr Tyr Leu Leu Glu Asn Pro His Gln Pro Ala Ser Leu Gln
225                 230                 235                 240

Ala Ala Asp Ser Leu Gly Asn Thr Ala Leu His Ala Leu Val Met Ile
                245                 250                 255

Ala Asp Asn Ser Ala Glu Asn Ser Ala Leu Val Ile Arg Met Tyr Asp
             260                 265                 270

Ala Leu Leu Arg Ala Gly Ala Arg Leu Cys Pro Lys Val Gln Leu Glu
         275                 280                 285

Asp Ile Pro Asn Leu Gln Gly Leu Thr Pro Leu Lys Leu Ala Ala Lys
    290                 295                 300

Glu Gly Lys Ile Glu Ile Phe Arg His Ile Leu Gln Arg Glu Phe Ser
305                 310                 315                 320

Gly Pro Cys Gln Ser Leu Ser Arg Lys Phe Thr Glu Trp Cys Tyr Gly
                325                 330                 335

Pro Val Arg Val Ser Leu Tyr Asp Leu Ala Ser Val Asp Ser Trp Glu
             340                 345                 350

Glu Asn Ser Val Leu Glu Ile Ile Ala Phe His Cys Arg Ser Pro His
         355                 360                 365

Arg His Arg Met Val Val Leu Glu Pro Leu Asn Lys Leu Leu Gln Ala
    370                 375                 380

Lys Trp Asp Leu Leu Ile Pro Arg Phe Phe Asn Phe Leu Cys Tyr
385                 390                 395                 400
```

Leu Thr Tyr Met Phe Ile Phe Thr Ala Val Ala Tyr His Gln Pro Ala
                405                 410                 415

Leu Gly Lys Ala Phe Leu Pro Pro Thr Val Thr Gly Asp Ser Met
        420                 425                 430

Leu Leu Leu Gly His Ile Leu Ile Leu Leu Gly Gly Val Tyr Leu Leu
                435                 440                 445

Val Gly Gln Leu Trp Tyr Phe Trp Arg Arg Arg Leu Phe Ile Trp Ile
        450                 455                 460

Ser Phe Val Asp Ser Tyr Phe Glu Leu Leu Phe Leu Val Gln Ala Leu
465                 470                 475                 480

Leu Thr Val Leu Ser Gln Gly Leu Cys Phe Leu Ala Val Glu Trp Tyr
                485                 490                 495

Leu Pro Leu Leu Val Ser Ser Leu Val Leu Gly Trp Leu Asn Leu Leu
        500                 505                 510

Tyr Tyr Thr Arg Gly Leu Gln His Thr Gly Ile Tyr Ser Val Met Ile
        515                 520                 525

Gln Lys Val Ile Leu Arg Asp Leu Leu Arg Phe Leu Leu Val Tyr Leu
        530                 535                 540

Val Phe Leu Phe Gly Phe Ala Val Ala Leu Val Ser Leu Ser Arg Glu
545                 550                 555                 560

Ala Arg Asp Ser Gly Val Pro Thr Gly Pro Asn Val Thr Glu Ala Ala
                565                 570                 575

Gln Ser Gly Ala Gly Gln Gly Asp Glu Gly Ser Ser Pro Tyr
        580                 585                 590

Gly Gly Ile Leu Asp Ala Ser Leu Glu Leu Phe Lys Phe Thr Ile Gly
        595                 600                 605

Met Gly Glu Leu Ala Phe Gln Asp Gln Leu Arg Phe Arg Gly Val Val
        610                 615                 620

Leu Leu Leu Leu Leu Ala Tyr Val Leu Leu Thr Tyr Ile Leu Leu Leu
625                 630                 635                 640

Asn Met Leu Ile Ala Leu Met Ser Glu Thr Val Asn Ser Val Ala Ser
                645                 650                 655

Asp Ser Trp Ser Ile Trp Lys Leu Gln Lys Ala Ile Ser Val Leu Glu
        660                 665                 670

Met Glu Asn Gly Tyr Trp Trp Cys Arg Arg Lys Lys Gln Arg Ala Gly
        675                 680                 685

Val Lys Leu Thr Val Gly Thr Arg Pro Asp Gly Ser Ser Asp Glu Arg
        690                 695                 700

Trp Cys Phe Arg Val Glu Glu Val Asn Trp Ala Ala Trp Glu Gln Thr
705                 710                 715                 720

Leu Pro Thr Val Cys Glu Glu Pro Ser Gly Pro Ala Val Pro Gly Ser
                725                 730                 735

Ile Arg Asn Pro Val Leu Ala Ser Gln Pro Glu Glu Asp Thr Ala Ser
        740                 745                 750

Glu Glu Asp Gln Leu Pro Leu Gln Leu Leu Lys Ser His
        755                 760                 765

<210> SEQ ID NO 3
<211> LENGTH: 2295
<212> TYPE: DNA
<213> ORGANISM: Homo sapiens

<400> SEQUENCE: 3
atgacctcac cctccagctc tccagttttc aggttggaga cattagatgg aggccaagaa      60
gatggctctg aggcggacag aggaaagctg gattttggga gcgggctgcc tcccatggag     120

```
tcacagttcc agggcgagga ccggaaattc gcccctcaga taagagtcaa cctcaactac      180
cgaaagggaa caggtgccag tcagccggat ccaaaccgat ttgaccgaga tcggctcttc      240
aatgcggtct cccggggtgt ccccgaggat ctggctggac ttccagagta cctgagcaag      300
accagcaagt acctcaccga ctcggaatac acagagggct ccacaggtaa gacgtgcctg      360
atgaaggctg tgctgaacct taaggacgga gtcaatgcct gcattctgcc actgctgcag      420
atcgacaggg actctggcaa tcctcagccc ctggtaaatg cccagtgcac agatgactat      480
taccgaggcc acagcgctct gcacatcgcc attgagaaga ggagtctgca gtgtgtgaag      540
ctcctggtgg agaatggggc caatgtgcat gcccgggcct gcggccgctt cttccagaag      600
ggccaaggga cttgctttta tttcggtgag ctaccccctct ctttggccgc ttgcaccaag      660
cagtgggatg tggtaagcta cctcctggag aacccacacc agcccgccag cctgcaggcc      720
actgactccc agggcaacac agtcctgcat gccctagtga tgatctcgga caactcagct      780
gagaacattg cactggtgac cagcatgtat gatgggctcc tccaagctgg ggcccgcctc      840
tgccctaccg tgcagcttga ggacatccgc aacctgcagg atctcacgcc tctgaagctg      900
gccgccaagg agggcaagat cgagattttc aggcacatcc tgcagcggga gttttcagga      960
ctgagccacc tttcccgaaa gttcaccgag tggtgctatg gcctgtccg gtgtcgctg     1020 tatgacctgc ttctgtgga cagctgtgag agaaactcag tgctggagat cattgccttt     1080
cattgcaaga gcccgcaccg acaccgaatg gtcgttttgg agcccctgaa caaactgctg     1140
caggcgaaat gggatctgct catccccaag ttcttcttaa acttcctgtg taatctgatc     1200
tacatgttca tcttcaccgc tgttgcctac catcagccta ccctgaagaa gcaggccgcc     1260
cctcacctga agcggaggt tggaaactcc atgctgctga cgggccacat ccttatcctg     1320 ctaggggga tctacctcct cgtgggccag ctgtggtact ctggcggcg ccacgtgttc     1380 atctggatct cgttcataga cagctacttt gaaatcctct tcctgttcca ggccctgctc     1440
acagtggtgt cccaggtgct gtgtttcctg gccatcgagt ggtacctgcc cctgcttgtg     1500
tctgcgctgg tgctgggctg gctgaacctg ctttactata cacgtggctt ccagcacaca     1560
ggcatctaca gtgtcatgat ccagaaggtc atcctgcggg acctgctgcg cttccttctg     1620
atctacttag tcttccttttt cggcttcgct gtagccctgg tgagcctgag ccaggaggct     1680
tggcgccccg aagctcctac aggccccaat gccacagagt cagtgcagcc catggaggga     1740
caggaggacg agggcaacgg ggcccagtac aggggtatcc tggaagcctc cttggagctc     1800
ttcaaattca ccatcggcat gggcgagctg gccttccagg agcagctgca cttccgcggc     1860
atggtgctgc tgctgctgct ggcctacgtg ctgctcacct acatcctgct gctcaacatg     1920
ctcatcgccc tcatgagcga gaccgtcaac agtgtcgcca ctgacagctg gagcatctgg     1980
aagctgcaga aagccatctc tgtcctggag atggagaatg gctattggtg gtgcaggaag     2040
aagcagcggg caggtgtgat gctgaccgtt ggcactaagc cagatggcag ccccgatgag     2100
cgctggtgct tcagggtgga ggaggtgaac tgggcttcat gggagcagac gctgcctacg     2160
ctgtgtgagg acccgtcagg ggcaggtgtc cctcgaactc tcgagaaccc tgtcctggct     2220 tccctctccca aggaggatga ggatggtgcc tctgaggaaa actatgtgcc cgtccagctc     2280
ctccagtcca actga                                                     2295
```

<210> SEQ ID NO 4
<211> LENGTH: 764
<212> TYPE: PRT
<213> ORGANISM: Homo sapiens

<400> SEQUENCE: 4

```
Met Thr Ser Pro Ser Ser Pro Val Phe Arg Leu Glu Thr Leu Asp
 1               5                  10                  15
Gly Gly Gln Glu Asp Gly Ser Glu Ala Asp Arg Gly Lys Leu Asp Phe
             20                  25                  30
Gly Ser Gly Leu Pro Pro Met Glu Ser Gln Phe Gln Gly Glu Asp Arg
             35                  40                  45
Lys Phe Ala Pro Gln Ile Arg Val Asn Leu Asn Tyr Arg Lys Gly Thr
 50                  55                  60
Gly Ala Ser Gln Pro Asp Pro Asn Arg Phe Asp Arg Asp Arg Leu Phe
 65                  70                  75                  80
Asn Ala Val Ser Arg Gly Val Pro Glu Asp Leu Ala Gly Leu Pro Glu
                 85                  90                  95
Tyr Leu Ser Lys Thr Ser Lys Tyr Leu Thr Asp Ser Glu Tyr Thr Glu
                100                 105                 110
Gly Ser Thr Gly Lys Thr Cys Leu Met Lys Ala Val Leu Asn Leu Lys
             115                 120                 125
Asp Gly Val Asn Ala Cys Ile Leu Pro Leu Leu Gln Ile Asp Arg Asp
130                 135                 140
Ser Gly Asn Pro Gln Pro Leu Val Asn Ala Gln Cys Thr Asp Asp Tyr
145                 150                 155                 160
Tyr Arg Gly His Ser Ala Leu His Ile Ala Ile Glu Lys Arg Ser Leu
                165                 170                 175
Gln Cys Val Lys Leu Leu Val Glu Asn Gly Ala Asn Val His Ala Arg
             180                 185                 190
Ala Cys Gly Arg Phe Phe Gln Lys Gly Gln Gly Thr Cys Phe Tyr Phe
             195                 200                 205
Gly Glu Leu Pro Leu Ser Leu Ala Ala Cys Thr Lys Gln Trp Asp Val
             210                 215                 220
Val Ser Tyr Leu Leu Glu Asn Pro His Gln Pro Ala Ser Leu Gln Ala
225                 230                 235                 240
Thr Asp Ser Gln Gly Asn Thr Val Leu His Ala Leu Val Met Ile Ser
                245                 250                 255
Asp Asn Ser Ala Glu Asn Ile Ala Leu Val Thr Ser Met Tyr Asp Gly
             260                 265                 270
Leu Leu Gln Ala Gly Ala Arg Leu Cys Pro Thr Val Gln Leu Glu Asp
             275                 280                 285
Ile Arg Asn Leu Gln Asp Leu Thr Pro Leu Lys Leu Ala Ala Lys Glu
290                 295                 300
Gly Lys Ile Glu Ile Phe Arg His Ile Leu Gln Arg Glu Phe Ser Gly
305                 310                 315                 320
Leu Ser His Leu Ser Arg Lys Phe Thr Glu Trp Cys Tyr Gly Pro Val
                325                 330                 335
Arg Val Ser Leu Tyr Asp Leu Ala Ser Val Asp Ser Cys Glu Glu Asn
             340                 345                 350
Ser Val Leu Glu Ile Ile Ala Phe His Cys Lys Ser Pro His Arg His
             355                 360                 365
Arg Met Val Val Leu Glu Pro Leu Asn Lys Leu Leu Gln Ala Lys Trp
             370                 375                 380
Asp Leu Leu Ile Pro Lys Phe Phe Leu Asn Phe Leu Cys Asn Leu Ile
385                 390                 395                 400
Tyr Met Phe Ile Phe Thr Ala Val Ala Tyr His Gln Pro Thr Leu Lys
                405                 410                 415
```

```
Lys Gln Ala Ala Pro His Leu Lys Ala Glu Val Gly Asn Ser Met Leu
                420                 425                 430

Leu Thr Gly His Ile Leu Ile Leu Leu Gly Gly Ile Tyr Leu Leu Val
                435                 440                 445

Gly Gln Leu Trp Tyr Phe Trp Arg Arg His Val Phe Ile Trp Ile Ser
450                 455                 460

Phe Ile Asp Ser Tyr Phe Glu Ile Leu Phe Leu Phe Gln Ala Leu Leu
465                 470                 475                 480

Thr Val Val Ser Gln Val Leu Cys Phe Leu Ala Ile Glu Trp Tyr Leu
                485                 490                 495

Pro Leu Leu Val Ser Ala Leu Val Leu Gly Trp Leu Asn Leu Leu Tyr
                500                 505                 510

Tyr Thr Arg Gly Phe Gln His Thr Gly Ile Tyr Ser Val Met Ile Gln
                515                 520                 525

Lys Val Ile Leu Arg Asp Leu Leu Arg Phe Leu Leu Ile Tyr Leu Val
530                 535                 540

Phe Leu Phe Gly Phe Ala Val Ala Leu Val Ser Leu Ser Gln Glu Ala
545                 550                 555                 560

Trp Arg Pro Glu Ala Pro Thr Gly Pro Asn Ala Thr Glu Ser Val Gln
                565                 570                 575

Pro Met Glu Gly Gln Glu Asp Glu Gly Asn Gly Ala Gln Tyr Arg Gly
                580                 585                 590

Ile Leu Glu Ala Ser Leu Glu Leu Phe Lys Phe Thr Ile Gly Met Gly
                595                 600                 605

Glu Leu Ala Phe Gln Glu Gln Leu His Phe Arg Gly Met Val Leu Leu
610                 615                 620

Leu Leu Leu Ala Tyr Val Leu Leu Thr Tyr Ile Leu Leu Leu Asn Met
625                 630                 635                 640

Leu Ile Ala Leu Met Ser Glu Thr Val Asn Ser Val Ala Thr Asp Ser
                645                 650                 655

Trp Ser Ile Trp Lys Leu Gln Lys Ala Ile Ser Val Leu Glu Met Glu
                660                 665                 670

Asn Gly Tyr Trp Trp Cys Arg Lys Lys Gln Arg Ala Gly Val Met Leu
                675                 680                 685

Thr Val Gly Thr Lys Pro Asp Gly Ser Pro Asp Glu Arg Trp Cys Phe
                690                 695                 700

Arg Val Glu Glu Val Asn Trp Ala Ser Trp Glu Gln Thr Leu Pro Thr
705                 710                 715                 720

Leu Cys Glu Asp Pro Ser Gly Ala Gly Val Pro Arg Thr Leu Glu Asn
                725                 730                 735

Pro Val Leu Ala Ser Pro Pro Lys Glu Asp Glu Asp Gly Ala Ser Glu
                740                 745                 750

Glu Asn Tyr Val Pro Val Gln Leu Leu Gln Ser Asn
                755                 760

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgatgatcgc agacaactca gccgagaaca                                    30
```

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggacagctgg gcctgatggc tcttca                                          26

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gattttgccc tccttggcag ccag                                            24

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttgccagagt tccggtcgat ctgaagca                                        28

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tccaagacca gctgcgcttc cgcggcgt                                        28

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atggcctcgc cctccagctc tccca                                           25

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ttagtgggac ttcaggagct ggaggggc                                        28

<210> SEQ ID NO 12

-continued

```
<211> LENGTH: 52
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (52)
<223> OTHER INFORMATION: a, c, t, g, unknown or other

<400> SEQUENCE: 12
ttctagaatt cagcggccgc tttttttttt tttttttttt tttttttttt vn          52
```